(12) United States Patent
Altobelli et al.

(10) Patent No.: US 8,900,159 B2
(45) Date of Patent: Dec. 2, 2014

(54) SYSTEM, METHOD AND DEVICE FOR AIDING IN THE DIAGNOSIS OF RESPIRATORY DYSFUNCTION

(71) Applicant: DEKA Products Limited Partnership, Manchester, NH (US)

(72) Inventors: David E. Altobelli, Hollis, NH (US); Benjamin W. Jones, Jr., Bedford, NH (US); Derek G. Kane, Manchester, NH (US); Gregory R. Lanier, Jr., Merrimack, NH (US); Paul R. Marquis, Litchfield, NH (US); Eric M. Soederberg, Bedford, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 146 days.

(21) Appl. No.: 13/735,618

(22) Filed: Jan. 7, 2013

(65) Prior Publication Data
US 2013/0331724 A1    Dec. 12, 2013

Related U.S. Application Data

(63) Continuation of application No. 11/347,971, filed on Feb. 6, 2006, now Pat. No. 8,348,853.

(51) Int. Cl.
*A61B 5/08*    (2006.01)
*A61B 5/083*   (2006.01)
*A61B 5/087*   (2006.01)
*A61B 5/091*   (2006.01)
*A61B 5/00*    (2006.01)

(52) U.S. Cl.
CPC .................. *A61B 5/091* (2013.01); *A61B 5/083* (2013.01); *A61B 5/087* (2013.01); *A61B 5/082* (2013.01); *A61B 5/417* (2013.01)
USPC ........................................... 600/532; 600/529

(58) Field of Classification Search
USPC .......... 600/529, 531–533, 537, 538, 540, 543
See application file for complete search history.

(56) References Cited

U.S. PATENT DOCUMENTS

| | | | |
|---|---|---|---|
| 5,233,996 A * | 8/1993 | Coleman et al. | 600/529 |
| 2004/0039295 A1* | 2/2004 | Olbrich et al. | 600/538 |
| 2004/0210154 A1* | 10/2004 | Kline | 600/532 |

* cited by examiner

*Primary Examiner* — Michael D'Angelo
(74) *Attorney, Agent, or Firm* — James D. Wyninegar, Jr.

(57) ABSTRACT

A system and method for aiding in the diagnosis of a respiratory dysfunction is described. More particularly, a system and method for aiding in the diagnosis of one or more pulmonary embolisms is described. The system and method described herein include a plurality of sensors, a thermal control system, and a controller coupled to the plurality of sensors and the thermal control system for aiding in the diagnosis of a respiratory dysfunction.

20 Claims, 17 Drawing Sheets

SIDE CROSS SECTION

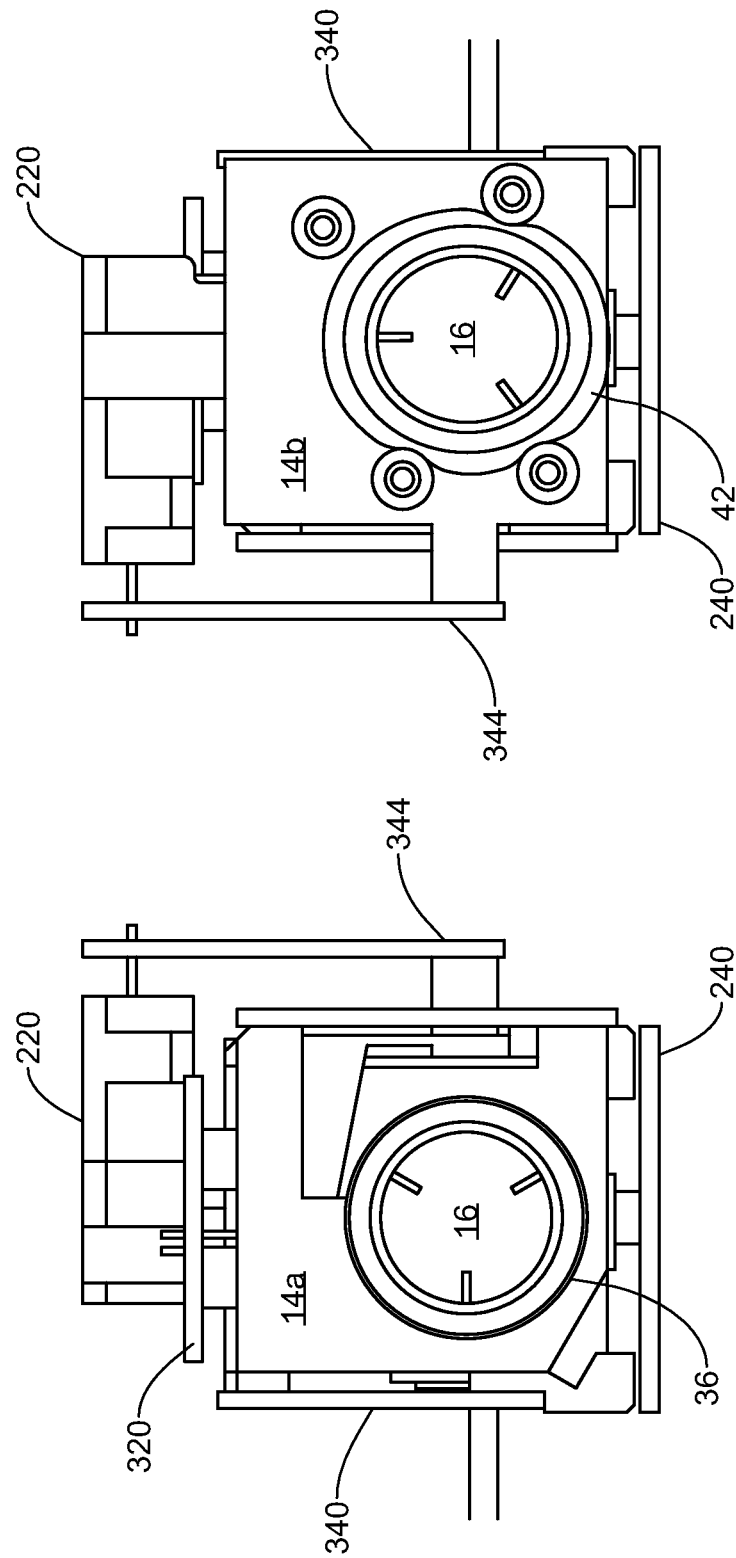

TOP VIEW

BOTTOM VIEW

BREATHQUANT ISOMETRIC
EXPLODED VIEW

OUTLET VIEW

INLET VIEW

TOP VIEW

BOTTOM VIEW

SYSTEM, METHOD AND DEVICE FOR AIDING IN THE DIAGNOSIS OF RESPIRATORY DYSFUNCTION

CROSS REFERENCE TO RELATED APPLICATIONS

The present application is a Continuation of patent application Ser. No. 11/347,971 filed Feb. 6, 2006 and entitled System, Method and Device for Aiding in the Diagnosis of Respiratory Dysfunction, now U.S. Published Application No. US-2007-0185405-A1 published Aug. 9, 2007, which is hereby incorporated herein by reference in its entirety.

FIELD OF THE INVENTION

The present invention relates to the field of medical devices and more particularly to the field of cardiovascular and pulmonary medicine.

BACKGROUND OF THE INVENTION

A pulmonary embolism occurs when an embolus become lodged in lung arteries, thus blocking blood flow to lung tissue. An embolus is usually a blood clot, known as a thrombus, but may also comprise fat, amniotic fluid, bone marrow, tumor fragments, or even air bubbles that block a blood vessel. Unless treated promptly, a pulmonary embolism maybe fatal.

A pulmonary embolism may be difficult to detect because signs and symptoms may vary depending on the severity of the occurrence. For instance, a pulmonary embolism may be confused with a heart attack, pneumonia, hyperventilation, congestive heart failure or a panic attack. In other cases, there may be no symptoms at all.

A physician will sometimes first eliminate the occurrence of other lung diseases before determining that the symptoms, if any, are caused by a pulmonary embolism. Traditional diagnostic methods of testing involve blood tests, chest X-rays, and electrocardiograms. These methods may typically be more effective in ruling out other possible problems than for actually diagnosing a pulmonary embolism. For example, a chest x-ray may reveal subtle changes in the blood vessel patterns after an embolism and signs of pulmonary infarction. However, chest x-rays may show normal lungs even when an embolism is present. Similarly, an electrocardiogram may show abnormalities that are mainly useful in establishing the possibility of a pulmonary embolism.

As a pulmonary embolism alters the ability of the lungs to oxygenate the blood and to remove carbon dioxide from the blood, one method of diagnosing the condition involves taking a specimen of arterial blood and measuring the partial pressure of oxygen and carbon dioxide in the arterial blood (i.e., an arterial blood gas analysis). Although a pulmonary embolism often causes abnormalities in these measurements, an individual finding or combination of findings from the arterial blood gas analysis does not necessarily provide a reliable way to exclude or a specific way of diagnosing a pulmonary embolism. For instance, some patients with a documented pulmonary embolism have normal oxygen and carbon dioxide contents of the arterial blood. Accordingly, the arterial blood analysis may not reliably include or exclude the diagnosis of a pulmonary embolism.

The blood D-dimer assay is another diagnostic method that has become available for commercial use. A D-dimer protein fragment is typically formed when fibrin is cleaved by plasmin and therefore produced naturally whenever clots form in the body. However, many studies have shown a D-dimer assay may produce a high degree of false positives.

In an attempt to increase the accuracy of diagnostic procedures for pulmonary embolisms, physicians have recently turned to methods that can produce an image of a potentially afflicted lung. One such method is a nuclear perfusion study that involves the injection of a small amount of radioactive particles into a vein. The radioactive particles then travel to the lungs where they highlight the perfusion of blood in the lung based upon whether they can penetrate a given area of the lung. However, one possible drawback with this method is that an abnormal scan does not necessarily mean that a pulmonary embolism is present.

Pulmonary angiograms are another means of diagnosing a pulmonary embolism. During a pulmonary angiogram, a catheter is threaded into the pulmonary artery so that iodine dye can be injected into the bloodstream. The dye flows into the regions of the lung and is imaged using x-ray technology, which may indicate a pulmonary embolism as a blockage of flow in an artery. Pulmonary angiograms may be useful in diagnosing pulmonary embolisms but often presents health risks and can be expensive. Spiral volumetric computed tomography is another diagnostic tool that has recently been proposed as a possibly less invasive test for detecting a pulmonary embolism. This procedure's reported sensitivity has varied widely, however, it may only be useful for diagnosing an embolism in the central pulmonary arteries, as it may be relatively insensitive to clots in more remote regions of the lungs.

The above-discussed pulmonary vascular imaging tests have several disadvantages in common. Many of the tests require ionizing radiation and invasiveness of, at a minimum, an intravenous catheter. Some tests also typically involve costs of more than $1,000 for the patient, take more than two hours to perform, and require special expertise such as a trained technician to perform the tests and acquire the images and a board-certified radiologist to interpret the images. Notably, many of the tests may not be completely safe for patients who are pregnant. As a result of these shortcomings, many of the imaging procedures currently used are not available in many outpatient clinic settings.

SUMMARY OF THE INVENTION

A system and method for aiding in the diagnosis of a respiratory dysfunction is described. More particularly, a system and method for aiding in the diagnosis of one or more pulmonary embolisms is described.

BRIEF DESCRIPTION OF THE DRAWINGS

FIG. 8 is an inlet view of the device of the present invention shown in FIG. 6.

FIG. 9 is an outlet view of the device of the present invention shown in FIG. 6.

DETAILED DESCRIPTION OF THE PREFERRED EMBODIMENTS

The present invention includes a comprehensive solution to the aforementioned problems associated with the state of the art. In particular, the device, system and associated methods of the present invention include mechanical and associated electronic means for ensuring the proper calibration and operation of the internal sensing components. Moreover, the system of the present invention is easily integrated with additional external sensors for further improving the data selection and diagnostic capabilities of the device. These and further benefits and advantages of the present invention are discussed in detail with reference to the Figures.

Figure 1:
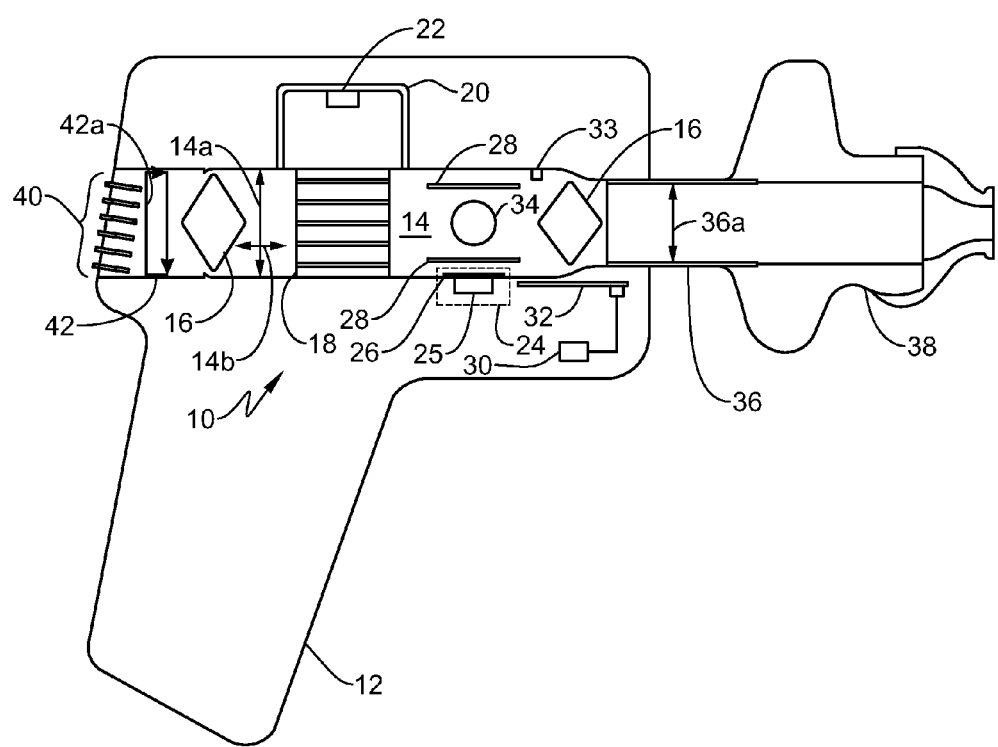
FIG. 1 is a schematic diagram of a medical device for aiding in the diagnosis of respiratory dysfunction in accordance with the present invention.

FIG. 1 is a schematic diagram of a medical device 10 for aiding in the diagnosis of respiratory dysfunction, more particularly in the diagnosis of a pulmonary embolism. As shown herein, the device 10 of the present invention may be encompassed within a housing 12 that forms a unitary combination of the numerous elements and subsystems of the present invention readily adaptable for use in a diagnostic situation. In the preferred embodiments, the device 10 of the present invention is a handheld unit, as shown in FIG. 1.

The device 10 generally includes an airway 14 that defines a diameter or cross-sectional dimension 14a substantially perpendicular to a longitudinal axis 14b. In preferred embodiments, the airway 14 is cylindrical in nature, with the longitudinal axis 14b being substantially the same as the flow of air while in use. The airway 14 is bounded at an inlet by an inlet adapter 36 and at an outlet at an outlet adapter 42. The inlet adapter 36 is also substantially cylindrical in nature, defining a diameter or cross-sectional dimension 36a that is substantially perpendicular to the longitudinal axis 14b. In preferred embodiments, the inlet diameter 36a is less than the airway diameter 14a, for reasons discussed in greater detail below. The outlet adapter 42 is also substantially cylindrical in nature, defining a diameter or cross-sectional dimension 42a that is substantially perpendicular to the longitudinal axis 14b. As in the prior instance, the outlet diameter 42a is preferably less than the airway diameter 14a.

The inlet adapter 36 is adapted for receiving a disposable mouthpiece 38 through which a patient may breath during use. Similarly, the outlet adapter 42 is in communication with an outlet port 40 that may be integral with the housing 12. In use, a patient breathes air in and out through the disposable mouthpiece 38, which causes the passage of inhaled air as well as exhaled air through the airway 14. As described more fully herein, the device 10 utilizes a plurality of sensors to analyze the content of the exhaled air in order to aid in the diagnosis of a respiratory dysfunction.

A pair of light restrictors 16 is disposed within the airway 14 proximal to the inlet adapter 36 and the outlet adapter 42. The light restrictors 16 shown herein generally define a symmetrical body having opposing convex surfaces that are oriented along longitudinal axis 14a of the airway 14. In preferred embodiments, the light restrictors 16 have a diameter that is less than that of the airway diameter 14a but greater than both the inlet adapter 36a and the outlet adapter 42a, respectively. In this manner, it is possible for air to flow through the airway 14 around the light restrictors 16, but light itself is unable to pass through the airway 14, thus protecting the internal sensors from interference or degradation, as discussed more fully below. Additionally, given the symmetrical convex shape of the light restrictors 16, a turbulent airflow that is drawn through the airway 14 becomes substantially laminar prior to its engagement with the plurality of sensors.

The device 10 further includes a flow restrictor 18 that is disposed in the airway 14 between the pair of light restrictors 16. The flow restrictor 18 is adapted for directing a portion of air into a flow bypass channel 20 that is in communication with a flow sensor 22. As shown in further detail below, the flow restrictor 18 forms a network of passages that cooperate to sufficiently occlude the airflow thereby directing air into the bypass channel and to the flow sensor 22. The flow restrictor 18 is preferably configured for insertion into the airway 14, and is thus preferably cylindrical in shape having a diameter substantially equal to that of the airflow diameter 14a.

The device 10 further includes an oxygen sensor 24 having an emitter/sensor 25 and a lens 26. The preferred oxygen sensor 24 is a combination of a light emitting diode (LED) and a photodetector that is adapted for measuring the reflectivity of the LED light off of a selected surface. In most preferred embodiments, the LED emits light in or around the blue wavelengths that is directed by the lens 26 onto a coated surface (not shown) that is reactive to oxygen. As the level of oxygen in the airflow varies, the fluorescence of the coated surface also varies and the photodetector measures this variance. Known relationships between the reflective intensity of the coated surface and the measured photodetector values are utilized to compute the amount of oxygen in the airflow.

The device 10 further includes a carbon dioxide sensor 34 that is disposed adjacent to the oxygen sensor 24 in the airway 14. The carbon dioxide sensor 34 is preferably a non-dispersive infrared sensor (NDIR), of the type known in the art.

According to the present invention, the oxygen sensor 24 and the carbon dioxide sensor 34 are arranged so as to minimize the potential for error in the computation of the oxygen to carbon dioxide ratio of the airflow. More particularly, the oxygen sensor 24 and the carbon dioxide sensor 34 are arranged so as to be mutually orthogonal with the longitudinal axis 14b. Or, as both sensors are preferably optical sensors, they are preferably arranged such that a first ray emanating from the oxygen sensor 24 and a second ray emanating from the carbon dioxide 34 sensor and the longitudinal axis 14b are mutually orthogonal. This orientation provides a number of benefits, including synchronized data collection over the same volume of air as it passes through the airway 14. Serial disposition of these sensors, as practiced in the state of the art, does not allow each sensor to operate independently upon the same volume of air at the same time, thus leaving open the possibility that changes in air temperature, flow direction, pressure or gaseous concentration will adversely affect the measured values of oxygen and carbon dioxide. The present invention solves this problem through the aforementioned orthogonal orientation of the oxygen sensor 24 and the carbon dioxide sensor 34.

A pair of substantially planar air deflectors 28 are disposed within the airway 14 to control the flow of air through the airway 14 as well as to prohibit any signal or optical interference between the oxygen sensor 24 and the carbon dioxide sensor 34. In preferred embodiments, the air deflector 28 disposed nearest the oxygen sensor 24 has a coated surface nearest the oxygen sensor 24, wherein the coated surface is optically sensitive to the presence of oxygen in the airflow. Alternatively, the coated surface can be placed on a disposable member (not shown) that can be removed from the device 10 and replaced without affecting the functionality of the oxygen sensor 24.

The device 10 of the present invention further contains temperature control means 30 including at least a first thermometer 31 and a heating element 32, wherein the latter two elements preferably cooperate to maintain the temperature of the airway 14 at a predetermined level. A second thermometer 33 is also preferably disposed within the airway 14 for measuring an air temperature as it passes there through. More specifically, variations in the temperature and relative humidity between inhaled air and exhaled air may cause unintended errors in the measurement of the oxygen to carbon dioxide ratios as measured by the present invention. Thus, while the first thermometer 31 and the heating element 32 cooperate to maintain a predetermined temperature on the airway surface 14, the second thermometer 32 is configured for measuring the temperature of the air passing through the heated airway 14.

The temperature control means 30 of the present invention is adapted for maintaining the temperature of the airway 14 at a range between thirty-three and forty-three degrees Celsius. More preferably, the temperature control means 30 of the present invention is adapted for maintaining the temperature of the airway 14 at approximately thirty-eight degrees Celsius.

The temperature control feature of the present invention provides a number of benefits, including removing any excess humidity from the exhaled air, warming the inhaled air so as to decrease the temperature gradient over the respiration cycle of a user, and increasing the sensitivity of the oxygen sensor 24 and the carbon dioxide sensor 34 by normalizing the relative humidity and temperature gradient over the respiration cycle.

Figure 2:
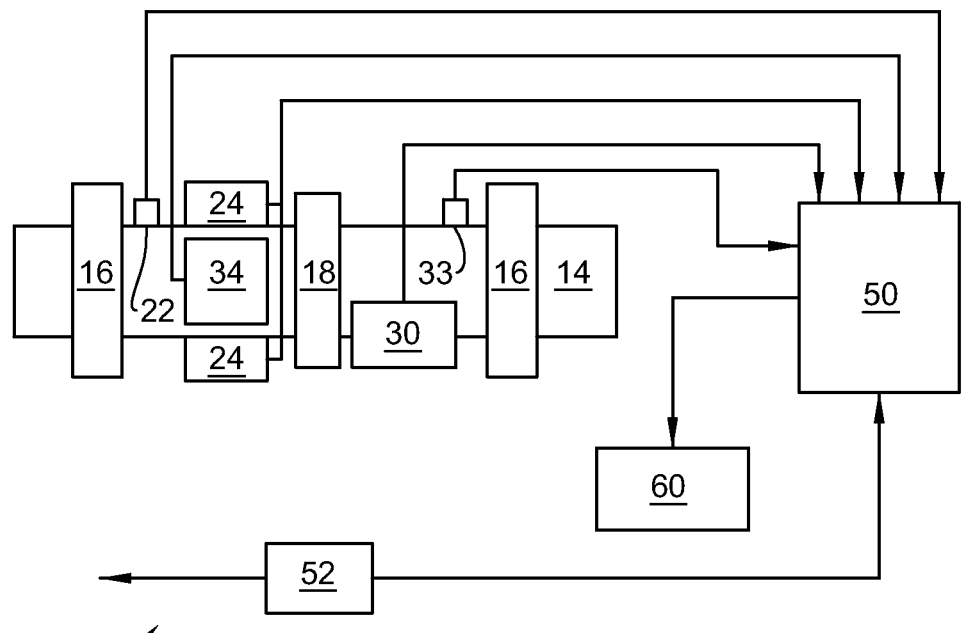
FIG. 2 is a schematic block diagram of a system for aiding in the diagnosis of respiratory dysfunction in accordance with the present invention.

The interaction of the various components of the present invention is also apparent in the block diagram of a system 100 according to the present invention shown in FIG. 2. The system 100 includes the airway 14, the light restrictors 16, and the flow restrictor 18 for managing the entry, exit and flow of the user's breadth as described above. Additionally, the system 100 includes the temperature control means 30, the oxygen sensor 24, the carbon dioxide sensor 34, the flow sensor 22 and the second thermometer 33, all of which are coupled through various means known in the art to a controller 50. The system 100 further includes a pulse meter 42 that is coupled to the controller 50 and is further adapted for communication with the user's body in order to determine the user's heart rate.

Each of the measuring components of the system input their respective data in real time to the controller 50, which is adapted for receiving such information and computing a ratio of oxygen to carbon dioxide in the user's breath, which in turn may be indicative of a pulmonary embolism. The controller thus receives data indicative of the total volume of air expelled by the patient, the oxygen content of the exhaled air, the carbon dioxide content of the exhaled air, the temperature of the exhaled air and the heart rate of the user. The data is processed by the controller according to the methodology described herein, and the results are transmitted to a display 60 coupled to the controller 50. The entire system 100 is adapted for use in a compact and mobile arrangement that is usable in a hospital environment. For example, a cart can be readily configured to include the controller 50 and display 60, the former of which can be adapted for interface with the device 10 and pulse meter 42 of the present invention in order to compile the system 100 described herein.

Figure 3:
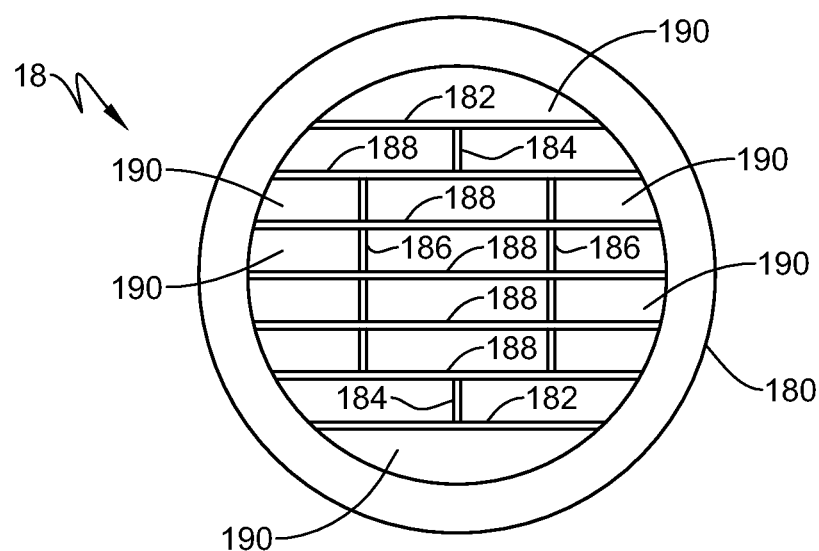
FIG. 3 is a front view of a flow restrictor usable in the device and system of the present invention.

As noted above, another novel aspect of the present invention is the flow restrictor 18 that is disposed in the airway 14 for directing air into the bypass channel 22, shown in the front view of FIG. 3. As shown herein, the flow restrictor 18 generally defines an annular edge portion 180 that is disposable within the airway 14. It should be understood that the flow restrictor 18 is annular in shape in order to fit within a cylindrical airway 14. In embodiments in which the airway 14 is non-cylindrical, the flow restrictor 18 will have a matching profile so as to prevent the flow of air between the edge portion 180 and the airway 14.

The flow restrictor 18 generally defines an interior space within the edge portion 180 that is divided into multiple portions by a plurality of substantially horizontal fins and substantially vertical fins. Preferably, the horizontal and vertical fins are oriented so as to be substantially mutually orthogonal with the longitudinal axis 14b, shown in FIG. 1. In the embodiment depicted in FIG. 3, a first pair of horizontal fins 182 are disposed opposite each other with a plurality of horizontal fins 188 disposed there between. Vertical fins 184, 186 bisect the horizontal fins 182, 188 as shown in order to define a plurality of openings 190 having substantially the same frontal area through which air may pass.

Although the shown combination of horizontal fins 182, 188 and vertical fins 184, 186 defines a plurality of openings 190 having a particular geometry, it should be understood by those skilled in the art that the size and shape of the plurality of openings 190 can be readily altered provided that there is a marked consistency across the surface of the flow restrictor 18. In operation, the flow restrictor 18 permits the flow of some air through the plurality of openings 190, while simultaneously causing a sufficient buildup in air pressure to divert the air into the bypass channel 20 shown in FIG. 1. Thus, for optimal performance the flow restrictor 18 should cause a uniform diversion of air without causing large deviations in the air pressure orthogonal to the longitudinal axis 14b so as to provide a consistent and steady flow of air into the bypass channel 20 to the flow sensor 22.

Figure 4A:
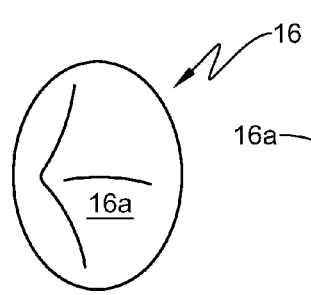
FIG. 4a is a perspective view of a light restrictor usable in the device and system of the present invention according to one embodiment.
Figure 4B:
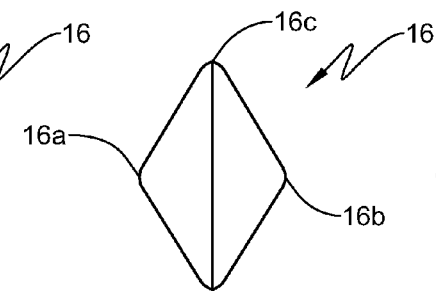
FIG. 4b is a side view of a light restrictor usable in the device and system of the present invention according to one embodiment.

The light restrictor 16 of the present invention is shown in two alternate embodiments in FIGS. 4a, 4b, 4c and 5a, 5b and 5c. In the first embodiment shown, the light restrictor 16 is generally defined by a body portion for substantially prohibiting the passage of light into the airway 14. FIG. 4a is a perspective view of the light restrictor 16 illustrating the contours of a leading edge 16a. As seen in the side view of FIG. 4b, the leading edge 16a and a trailing edge 16b are substantially symmetrical about the center 16c of the light restrictor 16.

As previously noted, the light restrictor 16 is adapted for use in the device 10 of the present invention, preferably being disposed at either end of the airway 14. In order to permit the passage of air while limiting or eliminating the passage of light into the airway 14, the diameter of the light restrictor 16 about its center 16c is preferably less than that of the airway 14 but greater than that of the respective inlet adapter 36 or outlet adapter 42.

The contours of the leading edge 16a and the trailing edge 16b are selected in order to maximize the efficient flow of air about the light restrictor 16 while minimizing any associated pressure drop along the trailing edge 16b. The aerodynamics of the light restrictor 16 have the added benefit of creating a laminar flow of the air as it passes through the airway 14, thereby increasing the consistency and dependability of the sensor measurements. The act of respiration may create large pockets of low pressure, and the typical airflow through any closed space maybe significantly turbulent. However, due to the specific design and shape of the light restrictor 16 described herein, a significant amount of that turbulence is eliminated in the process of restricting light entry into the airway 14.

Figure 4C:
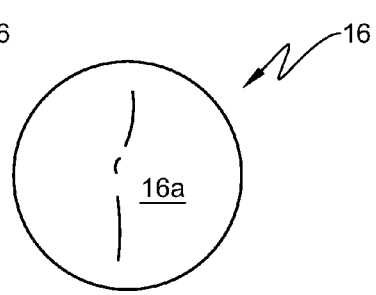
FIG. 4c is a front view of a light restrictor usable in the device and system of the present invention according to one embodiment.

The front view of FIG. 4c illustrates the substantially circular profile of the light restrictor 16. As discussed above with reference to the flow restrictor 18, it is conceivable that the airway will not have a cylindrical shape, and thus the cross-sectional profile of the light restrictor 16 may vary accordingly. Nevertheless, the functional aspects of the light restrictor 16 are the same in any embodiment or geometry. Namely, the light restrictor 16 of the present invention accomplishes two goals. First, the light restrictor 16 must substantially or entirely occlude any ambient light from irradiating the oxygen sensor 24 and its associated components. Secondly, the light restrictor 16 significantly reduces the turbulent flow of a user's breath through the airway 14 by adopting contours that will induce a laminar flow of air. The first goal is accomplished by appropriately sizing the diameter of the light restrictor 16 relative to that of the airway 14 and the inlet adapter 36 and outlet adapter 42. The second goal is accomplished as described above, by introducing a substantially symmetrical leading edge 16a and trailing edge 16 about a center 16c.

Figure 5A:
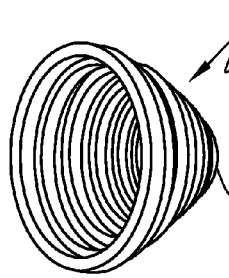
FIG. 5a is a perspective view of a light restrictor usable in the device and system of the present invention according to another embodiment.
Figure 5B:
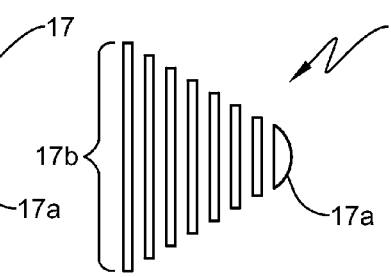
FIG. 5b is a side view of a light restrictor usable in the device and system of the present invention according to another embodiment.

FIG. 5a is a perspective view of a light restrictor 17 usable in the device and system of the present invention according to another embodiment. The light restrictor 17 depicted herein is generally conical in shape, consisting of a series of members arranged in order of decreasing size and terminating at a cap 17a. As shown in FIG. 5b, there are spaces between each successive member in the light restrictor 17, thus permitting significant airflow there through. However, as shown in FIG. 5c, the members are arranged radially about the cap 17a such that no light can be transmitted directly through the light restrictor 17, i.e. each successive member obstructs the passage of light through the larger adjacent member, and the cap 17a prevents light from passing directly along the longitudinal axis 14b.

Figure 5C:
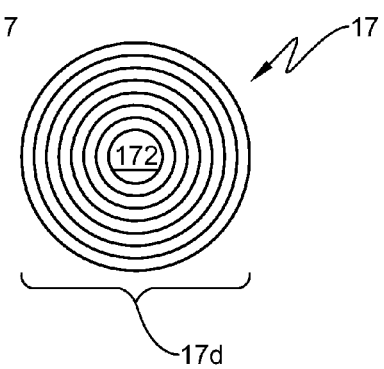
FIG. 5c is a front view of a light restrictor usable in the device and system of the present invention according to another embodiment.

As depicted in FIGS. 5a, 5b and 5c, this plurality of members of the light restrictor 17 is shown as a series of rings or annuli having a largest diameter 17b that is preferably coextensive with or less than the airway diameter 14a. Nevertheless, the light restrictor 17 described herein can take innumerable forms depending upon the cross-sectional profile of the airway 14. For an airway 14 that is cylindrical in nature, the most efficient and aerodynamic form for the light restrictor 17 would be a series of rings, as shown and described above. However, in the instances in which the airway 14 cross-section is square, elliptical or some other geometry, the specific shapes of the members can be varied accordingly to permit the passage of air with minimal pressure drop while prohibiting the entrance of light into the airway 14.

As described thus far, the present invention is a device and system arranged from various discreet components, including sensors, controlling means and the associated flow and light restrictors. However, the present invention includes numerous additional components that are preferred for its operation in the manner described herein. For example, the device and system of the present invention, in more preferred embodiments, include various integrated computation and electronic elements for efficiently receiving, analyzing and transmitting the data to the controller means 50.

Figure 6:
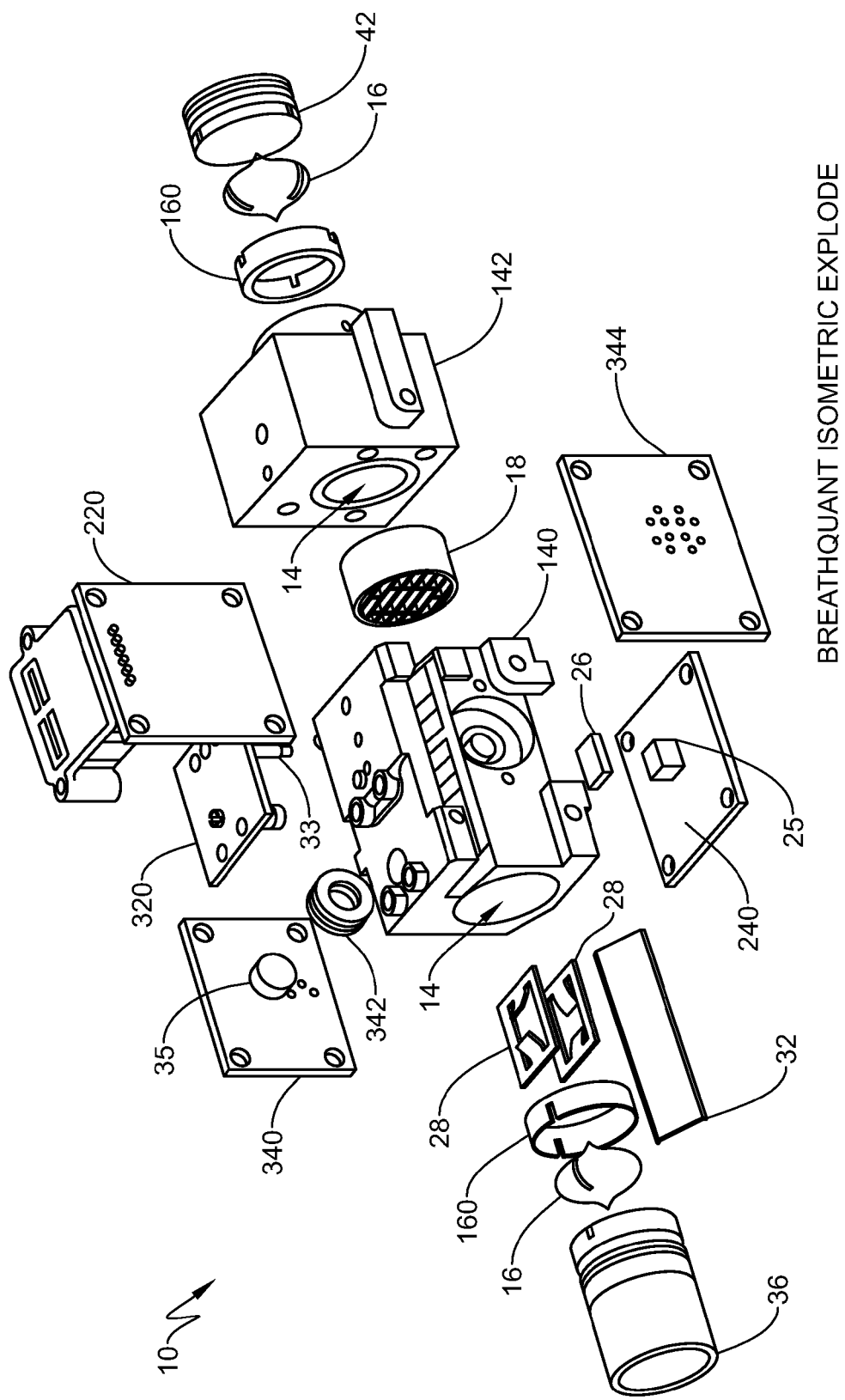
FIG. 6 is an exploded isometric view of the device of the present invention including additional components.
Figure 7:
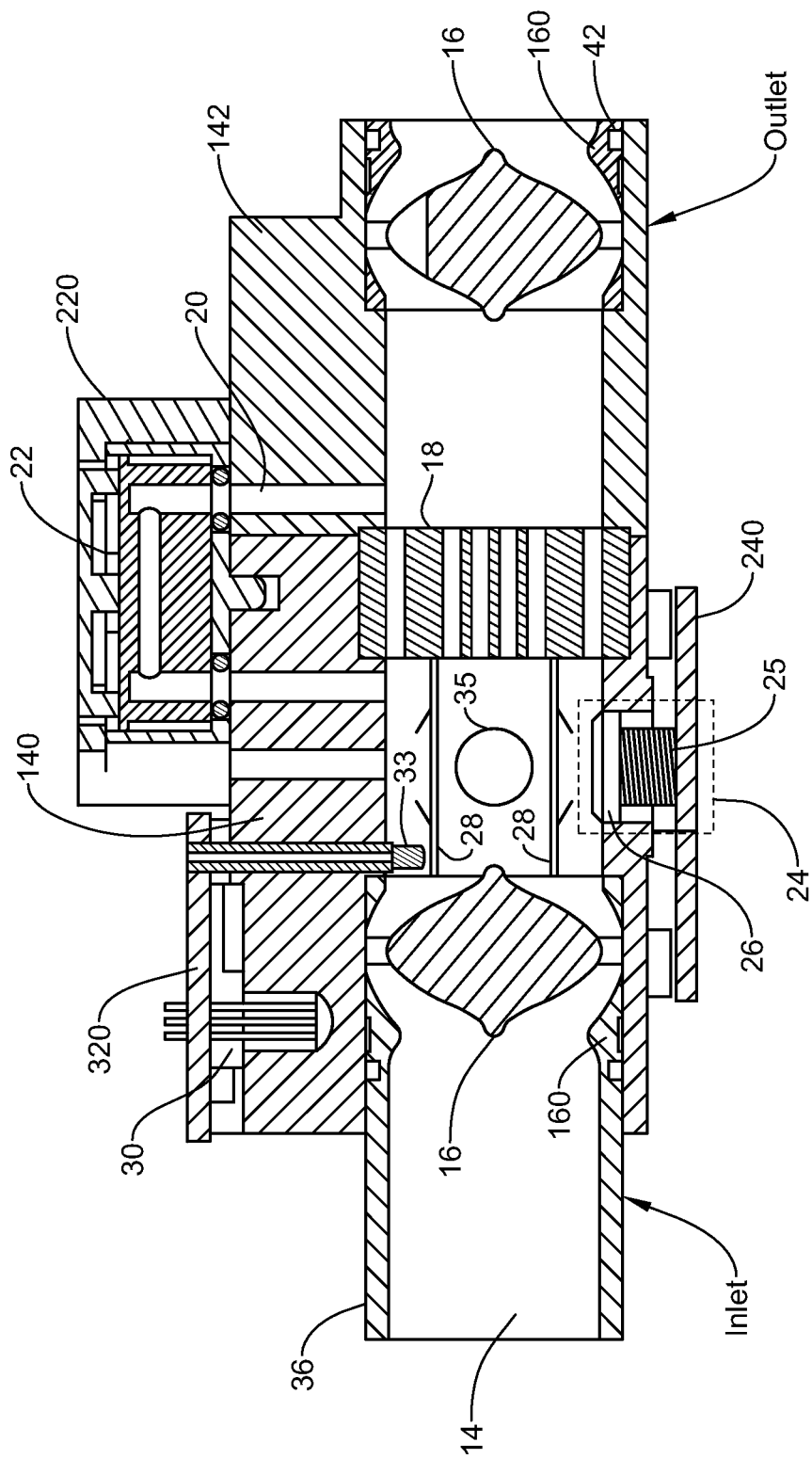
FIG. 7 is a cross sectional view of the device of the present invention shown in FIG. 6.
Figure 10:
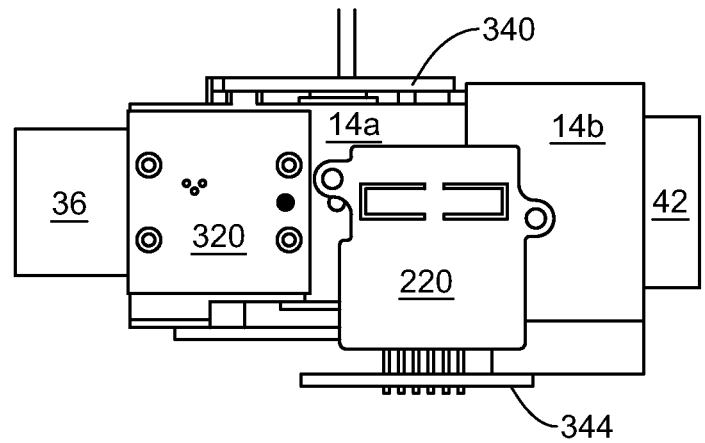
FIG. 10 is a top view of the device of the present invention shown in FIG. 6.
Figure 11:
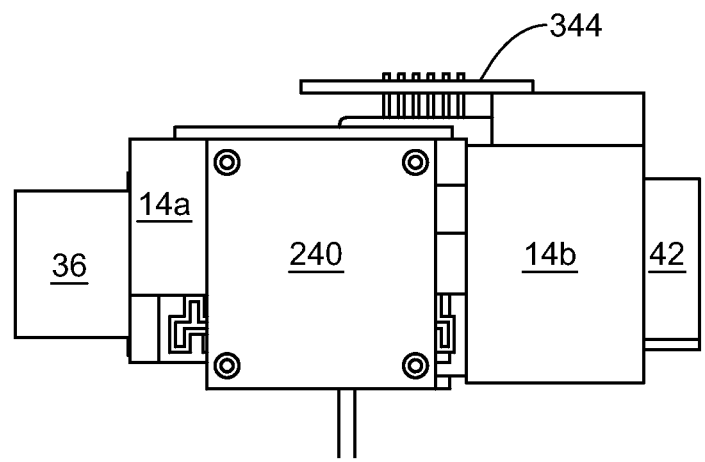
FIG. 11 is a bottom view of the device of the present invention shown in FIG. 6.

Another embodiment of the present invention is described herein with reference to FIGS. 6 through 11. FIG. 6 is an exploded isometric view of the device and system of the present invention including additional components useful in its preferred method of operation, and FIG. 7 is a cross-sectional view of the same. FIGS. 8 and 9 are inlet and outlet views of the device 10 of the present invention, respectively. FIGS. 10 and 11 are top and bottom views of the device described herein, respectively.

To the extent that identical reference numerals are used herein, they should be understood to refer to similar elements as previously described. As in the prior embodiment described above, the device 10 of the present invention generally includes an airway 14 that is defined in part by a first body portion 140 and a second body portion 142. The airway 14 contains, at or near the junction of the first body portion and the second body portion 142, a flow restrictor 18 of the type generally described herein.

The first body portion 140 receives at least one air deflector 28 disposed within the airway 14. A heating element 32, preferably integrated into the thermal control means described above with reference to FIGS. 1 and 2, is disposed within the first body portion 140 for maintaining the latter at a predetermined temperature. A light restrictor cradle 160 and a light restrictor 16 are also disposed within the airway 14 defined by the first body portion 140. The light restrictor cradle 160 serves multiple functions, including maintaining the orientation and placement of the light restrictor 16, as well as varying the diameter within the airway 14 such that light may not pass there through. Finally, an inlet adapter 36 is disposed within the airway 14 defined by the first body portion 140, to which a mouthpiece or other breathing apparatus may be attached during use.

The first body portion 140 shown herein also contains, is coupled to, or receives a number of sensors and subsystems noted above. In particular, the first body portion 140 includes receiving ports for receiving the carbon dioxide sensor 34, the flow sensor 22, the oxygen sensor 24, and the temperature control means 30, including the second thermometer 33 disposable within the airway 14, as shown in FIG. 1. Additionally, the first body portion 140 includes openings or tunnels that are formative of the flow bypass channels 20, described in detail above.

Each of the aforementioned sensors is coupled to or integrated with its associated electronic components, including for each sensor the necessary circuitry and processing means for converting raw signals sensed by the sensors into electronic signals that are adapted for processing by the controller 50 of the system 100 described above. Each of the sensors within the device 10 are thus readily connectable to the controller 50, shown in FIG. 2, through wired or wireless communications means known to those skilled in the art.

For example, as shown in FIG. 7 the oxygen sensor 24 and its components, the emitter/sensor 25 and the lens 26, are shown integrated into an oxygen sensor printed circuit board (PCB) 240 that is attachable to the first body portion 140 as shown. Similarly, the flow sensor 22 and its associated structure is shown integrated into a flow sensor PCB that is attachable to the first body portion 140, preferably on a side opposite to that of the oxygen sensor PCB 240. The temperature control means 30 and its associated components, including the second thermometer 33, are shown integrated into a temperature control PCB 320, which again is preferably disposed on a side of the first body portion 140 opposite to that of the oxygen sensor PCB 240.

The carbon dioxide sensor 34 is preferably dual-sided in nature, having both an emitter side and a detector side. Thus, the carbon dioxide sensor 34 consists of a carbon dioxide sensor emitter PCB 340, including a carbon dioxide sensor emitter 35, and a carbon dioxide detector PCB 344, including a carbon dioxide detector (not shown). In order to prevent interference between the oxygen sensor 24 and the carbon dioxide sensor 34, it is preferable to dispose the respective carbon dioxide PCBs 340, 344 on opposing sides of the first body portion 140 that are adjacent to the oxygen sensor PCB 240. In preferred embodiments, the device further includes at least one carbon dioxide sensor adaptor 342 for affixing the carbon dioxide PCBs 340, 344 that serve the further purpose of protecting the optical components of the carbon dioxide sensor 34.

The second body portion 142 also defines a portion of the airway 14. The second body portion 142 also is adapted to receive a light restrictor cradle 160 and a light restrictor 16, both of which are buttressed on a distal end by an outlet adapter 42. As previously noted, the light restrictor cradle 160 serves multiple functions, including maintaining the orientation and placement of the light restrictor 16, as well as varying the diameter within the airway 14 such that light may not pass there through.

Figure 12:
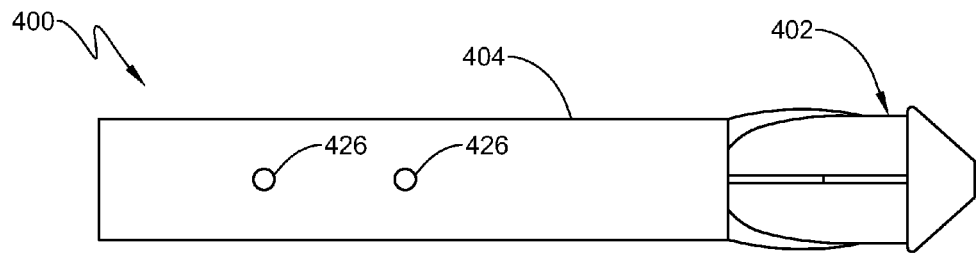
FIG. 12 is a top view of a disposable assembly in accordance with the present invention.
Figure 13:
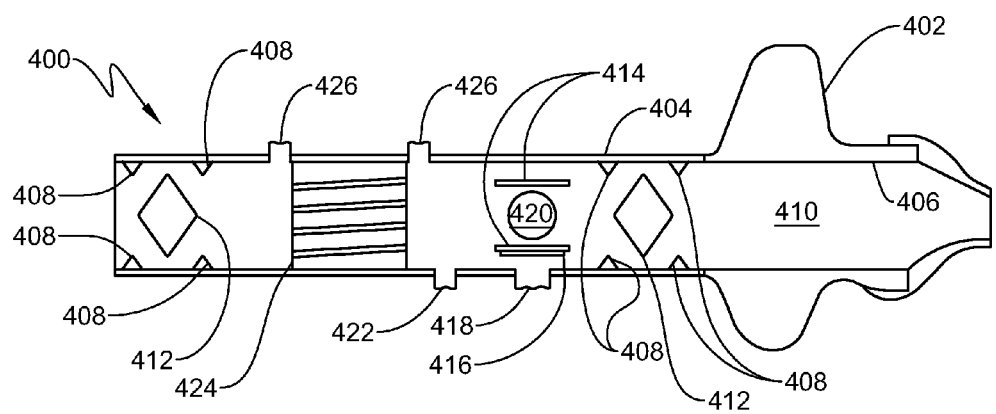
FIG. 13 is a side cross-sectional view of the disposable assembly shown in FIG. 12.
Figure 14:
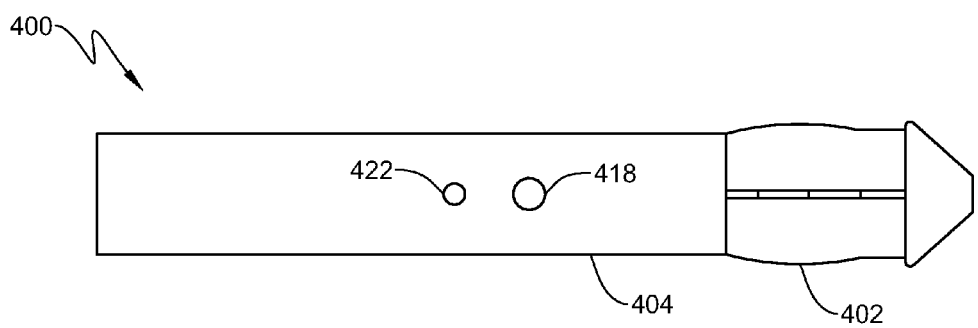
FIG. 14 is a bottom view of the disposable assembly shown in FIG. 13.

In another aspect of the present invention, a disposable assembly is provided that integrates the necessary airflow and light restriction features while maintaining the functional aspects associated with the device and system outlined above. FIGS. 12, 13 and 14 are top, cross-sectional, and bottom views of the assembly 400 in accordance with a preferred embodiment.

Referring to FIGS. 12, 13 and 14 simultaneously, it is shown that the assembly 400 includes an airway 404 that is coupled to a mouthpiece 402. In some embodiments, the airway 400 and the mouthpiece may be selectively coupled, such that each component can be separately sterilized or disposed of following use. Alternatively, the assembly 400 can be readily designed as an integrated whole that is disposable after each and every use.

As seen best in FIG. 13, the airway 404 defines an interior volume that contains a number of elements described above. The mouthpiece 402 defines an inner surface 406 defining a first volume 410 across a first diameter. Entrance into the interior of the airway 14 is partially obstructed by a light restrictor 412 that is bounded on either side by a pair of ridges 408. The opposing light restrictor 412 is also bounded by a pair of ridges 408 disposed along the interior of the airway 404. The respective ridges 408 function to prevent the passage of light into the interior of the airway 404 while simultaneously cooperating with the light restrictor 412 to permit the regular and laminar flow of air there through. As in prior embodiments, the ridges 408 may be designed as light restrictor cradles or changes in the shape of the interior of the airway 404. Likewise, it should be understood that different types of light restrictors, such as those described herein, might also be used in the assembly 400 of the present invention.

A flow restrictor 424 is disposed within the airway 404 between the light restrictors 412. As in prior preferred embodiments, the airway 404 is also populated by a pair of air deflectors 414. The air deflectors 414 are arranged about a first sensor window 420, as shown in FIG. 13. In preferred embodiments, the sensor window is alignable with an optical sensor, such as a carbon dioxide sensor, which requires the further presence of the air deflectors 414 to avoid any interference with other optical sensors operating in the airway 404.

The airway 414 further defines a second sensor window 418 that is disposed opposite one of the air deflectors 414. In preferred embodiments, the second sensor window 418 is alignable with a second optical sensor, such as for example an oxygen sensor. In such an embodiment, it is further possible to dispose an oxygen-sensitive surface 416 on the near surface of the opposing air deflector 416. As previously noted, in the operation of both an oxygen and a carbon dioxide sensor, it is preferable for the air deflectors 414 to be aligned in such a manner so as to prevent any optical interference between the sensors.

The airway 414 further defines a first sensor port 422 disposed along the bottom of the airway 414 as shown in FIGS. 13 and 14. The first sensor port 422 is preferably adapted for a thermometer or other means for measuring the temperature of air that is passing through the airway 414. A set of second ports 426 visible in FIGS. 12 and 13, are disposed about the flow restrictor 424 for permitting the selective passage of air out of the airway 404. In preferred embodiments, the second ports 426 are alignable with a flow sensor of the type described herein in which air is directed through a bypass channel.

Figure 15:
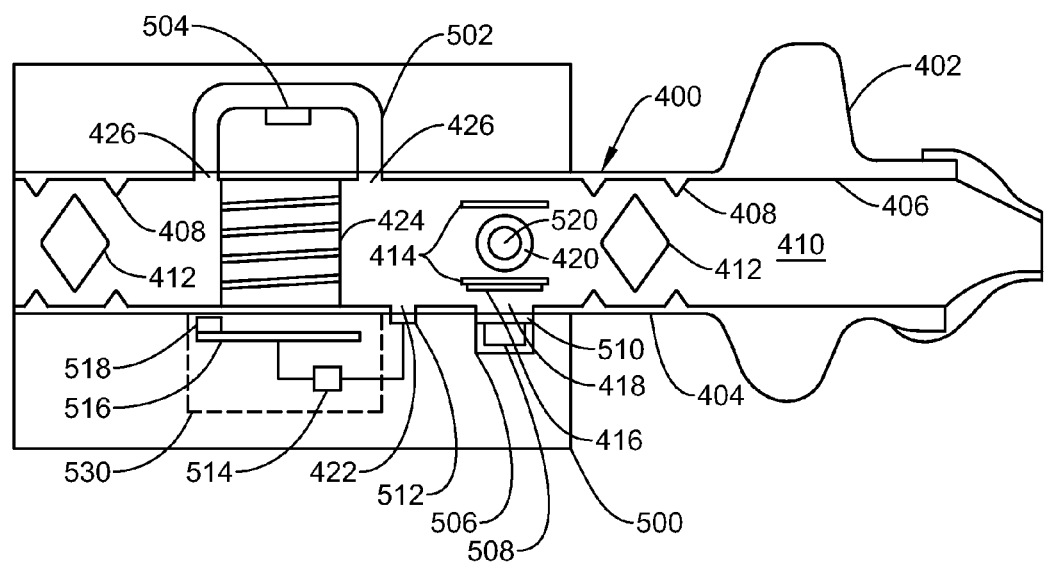
FIG. 15 is a cross-sectional view of the disposable assembly of the present invention in use with an electronic device of the present invention.

In its more preferred embodiments, the assembly 400 of the present invention is utilized in conjunction with an electronic device 500 as shown in FIG. 15. The assembly 400, including each of the features described above, is shown inserted into a receptacle formed within an electronic device 500. The electronic device 500 includes a bypass channel 502 that is in fluid communication with a flow sensor 504. In preferred embodiments, the bypass channel 502 is readily and automatically aligned with the second ports 426 of the airway 404 such that air passing through the airway 404 is diverted into the bypass channel 502 by the flow restrictor 424. It is further preferred that the junction between the second ports 426 and the bypass channel 502 is substantially airtight so as to cause minimal disruption in the airflow through the airway 404.

The electronic device 500 shown herein further includes an oxygen sensor 506 including an emitter/detector 508 and a lens 510 that are disposed within the electronic device 500 adjacent to the second sensor window 418. In preferred embodiments, the oxygen sensor 506 is oriented within the electronic device 500 such that placement of the assembly 400 therein automatically aligns the oxygen sensor 506 with the oxygen sensitive surface 416 located within the airway 404.

The electronic device 500 also includes a carbon dioxide sensor 520 that is disposed therein such that insertion of the assembly 400 causes the carbon dioxide sensor 520 to be automatically aligned with the first sensor window 420. Both the first sensor window 420 and the second sensor window 418 are preferably composed of a material that is optically transparent across the spectra used by the respective sensors. Moreover, it is preferable for the first sensor window 420 and the second sensor window 418 to be airtight so as to substantially minimize any disruption in the airflow through the airway 404.

The first port 422 is in fluid communication with a thermometer 512 for measuring a temperature of the air passing through the airway 404. The first port 422 is preferably sealed against the thermometer 512 in an airtight fashion so as to substantially eliminate any turbulence in the airflow through the airway 404.

A temperature control system 530 including a temperature controller 514, a heating element 516 and a second thermometer 518 is preferably disposed within the electronic device. In operation, the temperature control system 530 serves to maintain the electronic device 500 at a specified temperature. Thermal induction will further ensure that the airway 404, when properly inserted within the electronic device 500, will also be maintained at or about the specified temperature. In particular, it is desirable to maintain the airway 404 at a temperature of between thirty-three and forty-three degrees Celsius, although it is even more preferable to maintain a temperature of approximately thirty-eight degrees Celsius.

The benefits of temperature control within the present invention are described above including, without limitation, warming the inhaled air so as to decrease the temperature gradient over the respiration cycle of a user, and increasing the sensitivity of the oxygen sensor 506 and the carbon dioxide sensor 520 by normalizing the relative humidity and temperature gradient over the respiration cycle.

Figure 16:
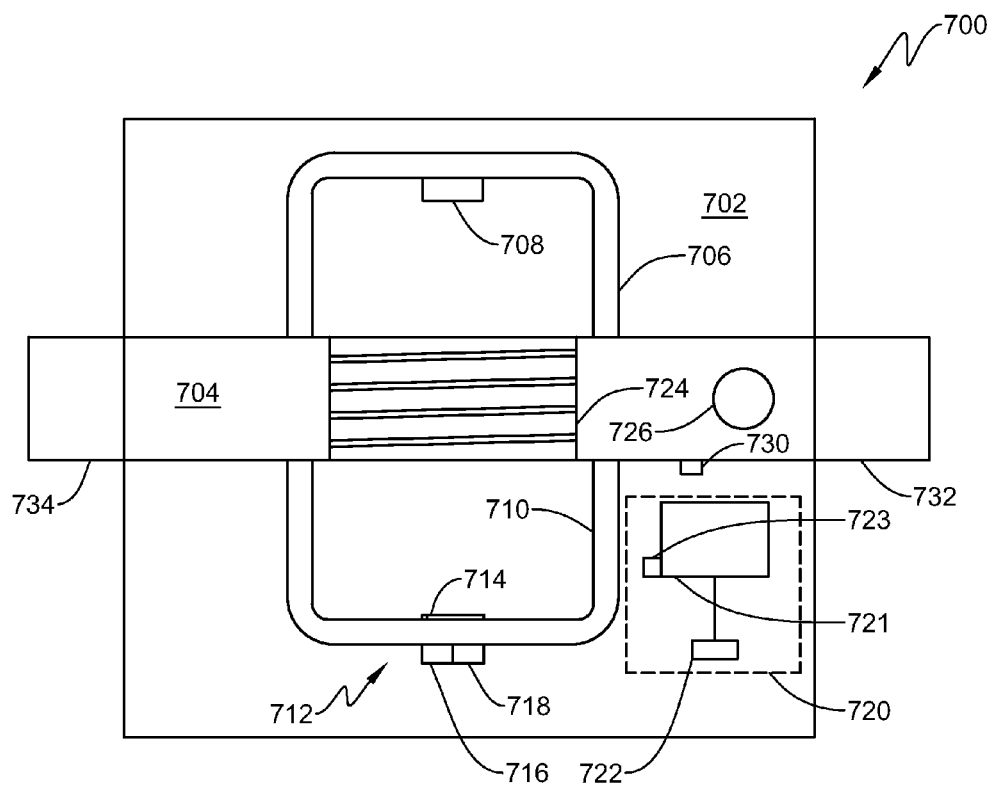
FIG. 16 is a side cross-sectional view of a medical device for aiding in the diagnosis of a respiratory dysfunction in accordance with the present invention.
Figure 17:
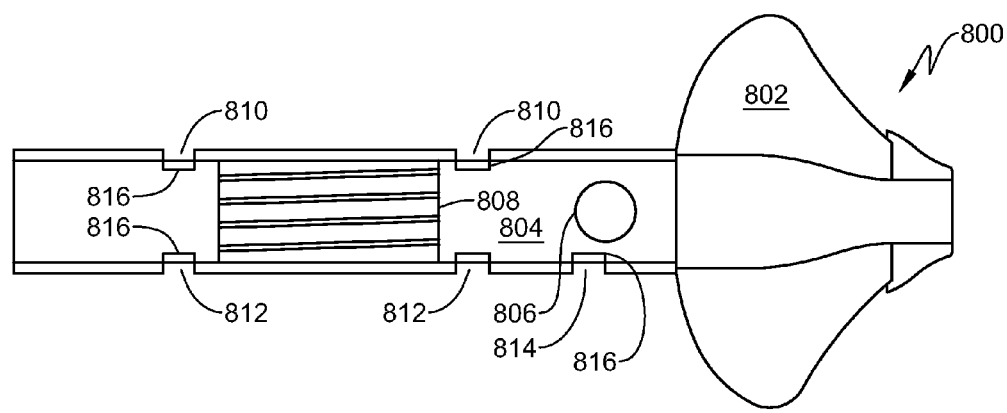
FIG. 17 is a side cross-sectional view of a disposable assembly of usable in conjunction with an electronic device in accordance with the present invention.

Another aspect of the present invention is shown in FIGS. 16 and 17 in which the oxygen sensor is located within a second bypass channel. As shown herein, a device 700 is shown for aiding in the determination of a pulmonary dysfunction. The device 700 generally includes a body portion 702 defining an airway 704 there through. The airway 704 is bounded on one end by an inlet adapter 732 and on another end by an outlet adapter 734. A flow restrictor 724 of the type described above is disposed within the airway 704. In operation, the flow restrictor 724 diverts a selected portion of each inhaled and exhaled breath into a first bypass channel 706 and a second bypass channel 710.

A carbon dioxide sensor 726 of the type described above is disposed adjacent to the airway 704. Preferably, the carbon dioxide sensor 726 is optical in nature. A thermometer 730 is disposed in the airway 704 for measuring the temperature of the inhaled and exhaled breaths passing there through. As in prior embodiments, the device 700 also includes a temperature control means 720 including a heating element 721, a controller 722 and a second thermometer 723. As noted with respect to the prior embodiments, the temperature control means 720 is adapted for maintaining the device 700 in general and the airway in particular 704 at a specified minimum temperature. In particular, the temperature control means 720 serves to maintain the airway 704 at a temperature of between thirty-three and forty-three degrees Celsius, although it is even more preferable to maintain a temperature of approximately thirty-eight degrees Celsius.

The benefits of temperature control within the present invention are described above, including removing any excess humidity from the exhaled air, warming the inhaled air so as to decrease the temperature gradient over the respiration cycle of a user, and increasing the sensitivity of the oxygen sensor 712 and the carbon dioxide sensor 726 by normalizing the relative humidity and temperature gradient over the respiration cycle.

The first bypass channel 706 is adapted for diverting a portion of the airflow towards a flow sensor 708 of the type described in detail above. The second bypass channel 710 is adapted for diverting a portion of the airflow towards an oxygen sensor 712 of the type described above. In preferred embodiments, the oxygen sensor 712 includes an emitter 716, a detector 718 and an oxygen sensitive surface 714 disposed across the second bypass channel 710 such that light emitted from the emitter 716 is reflected from the oxygen sensitive surface 714 to the detector 718.

Unlike in prior embodiments in which the oxygen sensitive surface 714 was protected from ambient light through the use of mechanical light restrictors, the current embodiment of the present invention maintains the lifetime of the oxygen sensitive surface 714 by disposing it within the second bypass channel 710. The benefits of doing so are apparent to those skilled in the art, including the ease of engineering and designing the present embodiment without the use of light restrictors or labyrinths. Moreover, as the oxygen sensor itself 712 is disposed along the second bypass channel 710, the flow of air there through is readily measured and controlled according to the mechanical properties of the flow restrictor 724 and the operation of the flow sensor 708. Additionally, by eliminating the need for light restrictors, the overall volume of the airway 704 is lessened, therefore requiring less volume per breath in order to properly and consistently operate the sensors of the present invention. As noted in the current specification, it is a feature of the present invention that greater control and measurement precision over the relevant variables (flow, temperature, oxygen, carbon dioxide, and pulse rate) is instrumental in assuring accurate and predictive diagnosis of a respiratory dysfunction.

In yet another embodiment of the present invention, a disposable assembly 800 is shown in FIG. 17 that encompasses features of the aforementioned disposable assembly, but adapted for fitting into an electronic device having an oxygen sensor disposed in an ancillary bypass channel. As such, the assembly 800 includes a mouthpiece 802 that is selectively coupled to or integrated with an airway 804 defining a volume through which air may freely flow. A flow restrictor 808 is disposed within the airway 804 for directing a specified portion of the airflow into a pair of bypass channels, such as those described above with reference to FIG. 17.

A window 806 is also provided in the airway 804 that is readily and automatically alignable with a carbon dioxide sensor (not shown) disposed within the receiving device. Similarly, a first port 814 is provided for permitting access to the airway 804 by a thermometer (not shown) for measuring the air temperature of the airflow. The numerous benefits of air temperature measurement are described herein. A second set of ports 810 and a third set of ports 812 are disposed on opposing surfaces of the airway 804 in the manner shown in FIG. 17. In preferred embodiments, the second ports 810 and third ports 812 are readily aligned with a first and second bypass channel, each providing airflow to one of an oxygen sensor or a flow sensor, as described above.

It is another feature of the present invention that each of the first port 814, second ports 810, and third ports 812 are coverable by a filtration media 816 having microbial properties. In such a manner, a user can readily discard the assembly 800 of the present invention after each use without risk of directly exposing any electronic devices or sensors to a patient's breath.

Figure 18:
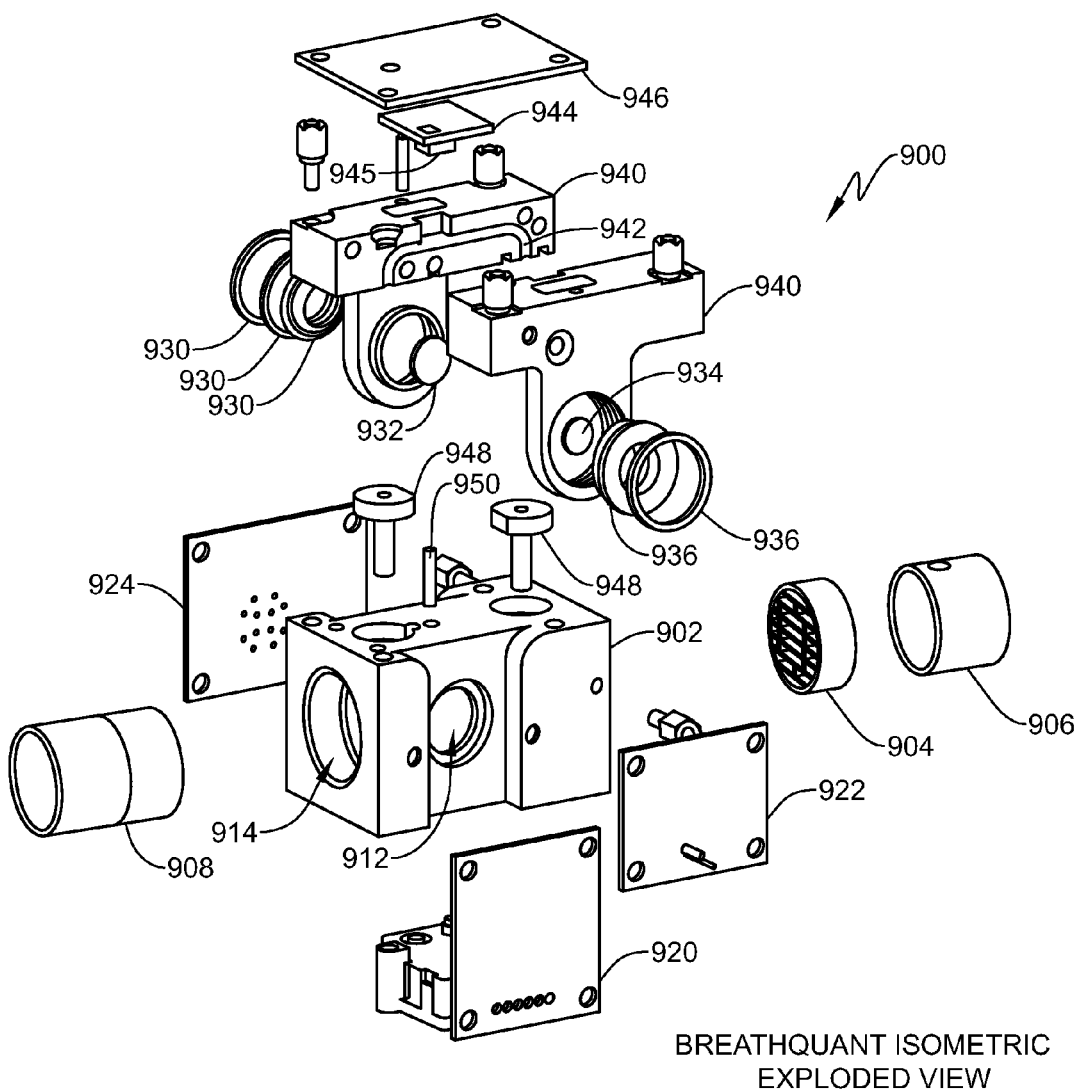
FIG. 18 is an isometric exploded view of a medical device for aiding the diagnosis of a respiratory dysfunction in accordance with the present invention.
Figure 19:
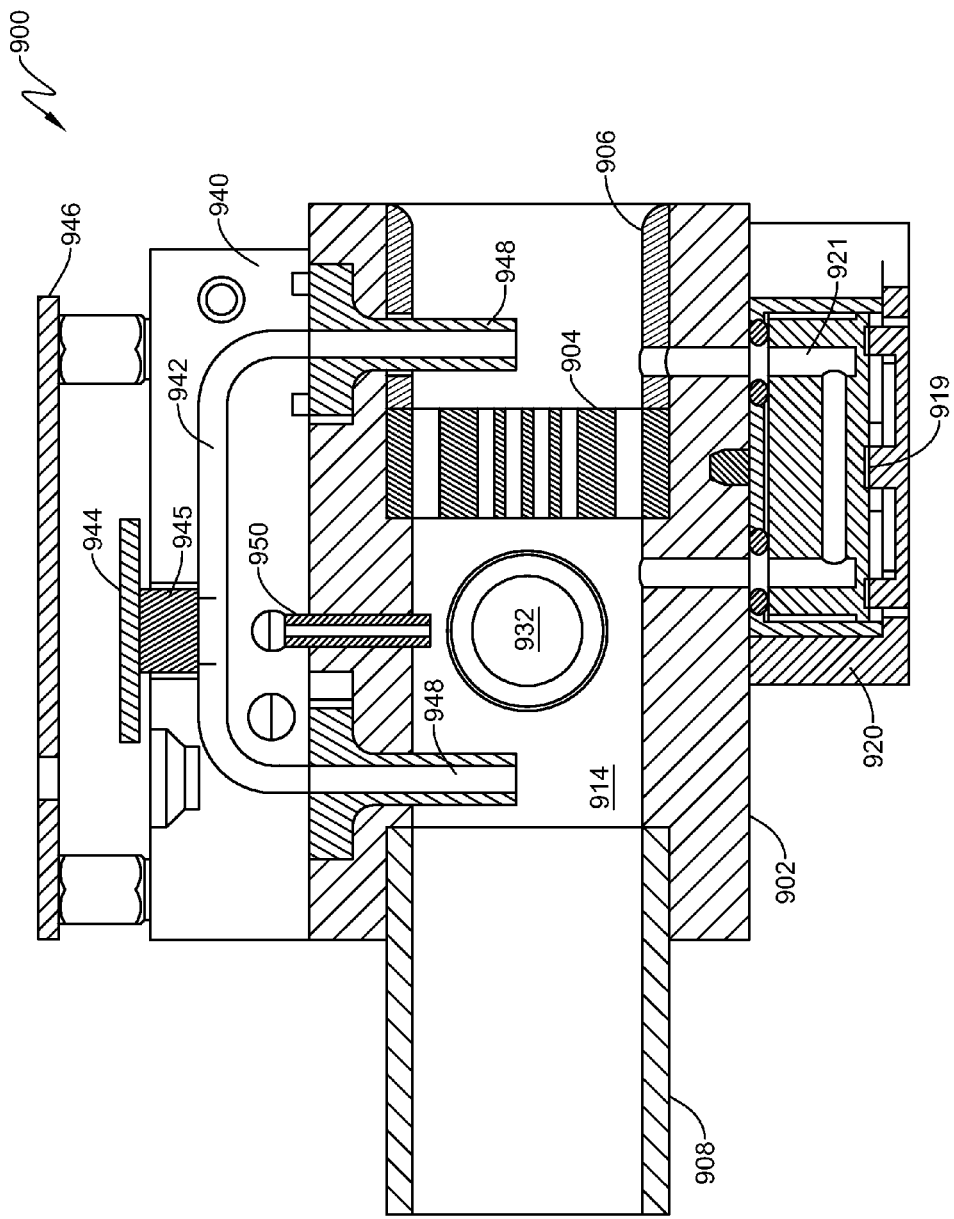
FIG. 19 is a side cross-sectional view of the device of the present invention shown in FIG. 18.
Figure 21:
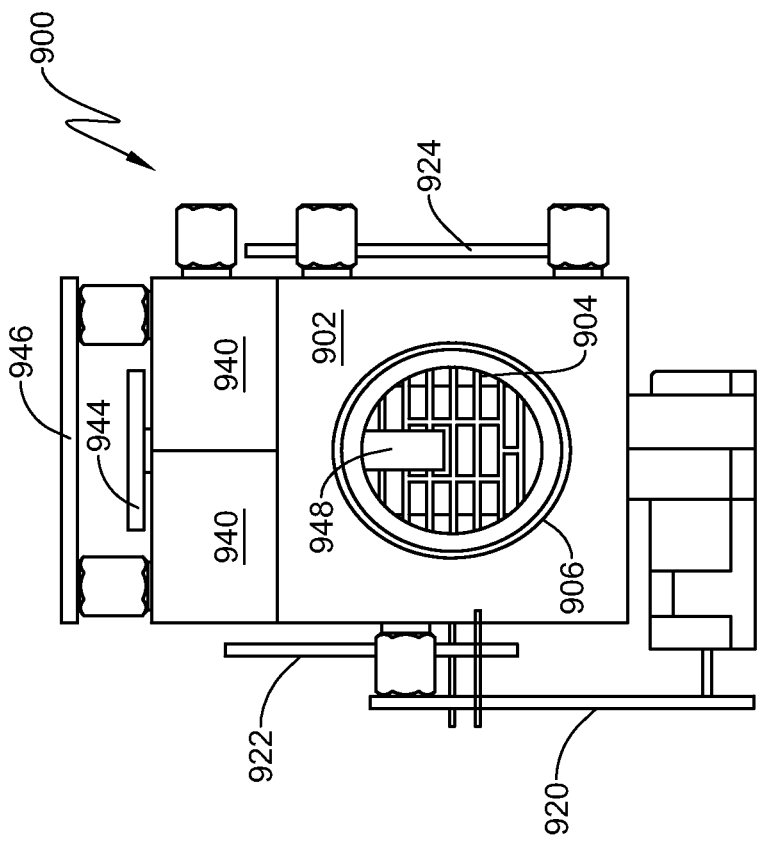
FIG. 21 is an outlet view of the device of the present invention shown in FIG. 18.
Figure 20:
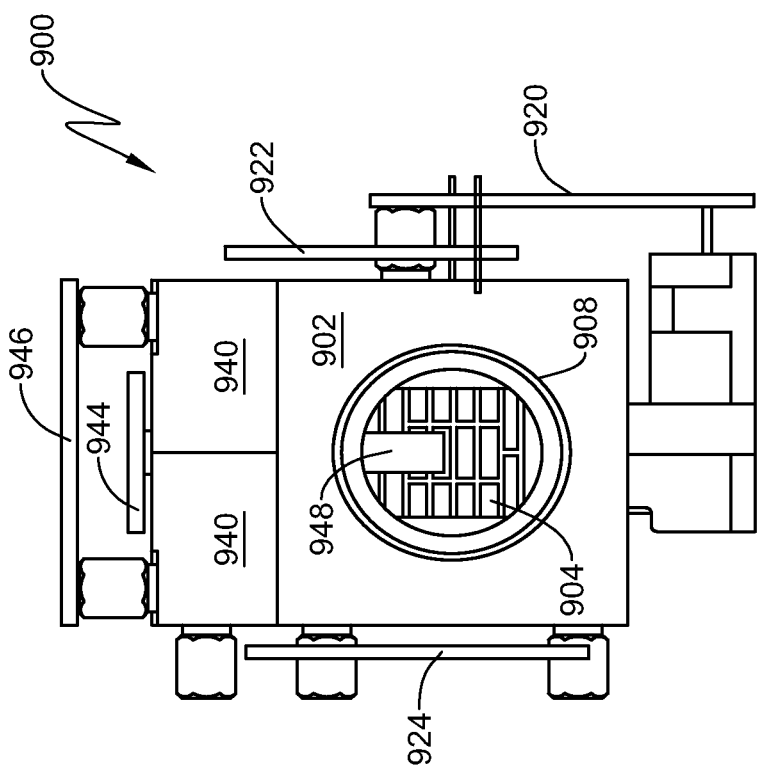
FIG. 20 is an inlet view of the device of the present invention shown in FIG. 18.
Figure 22:
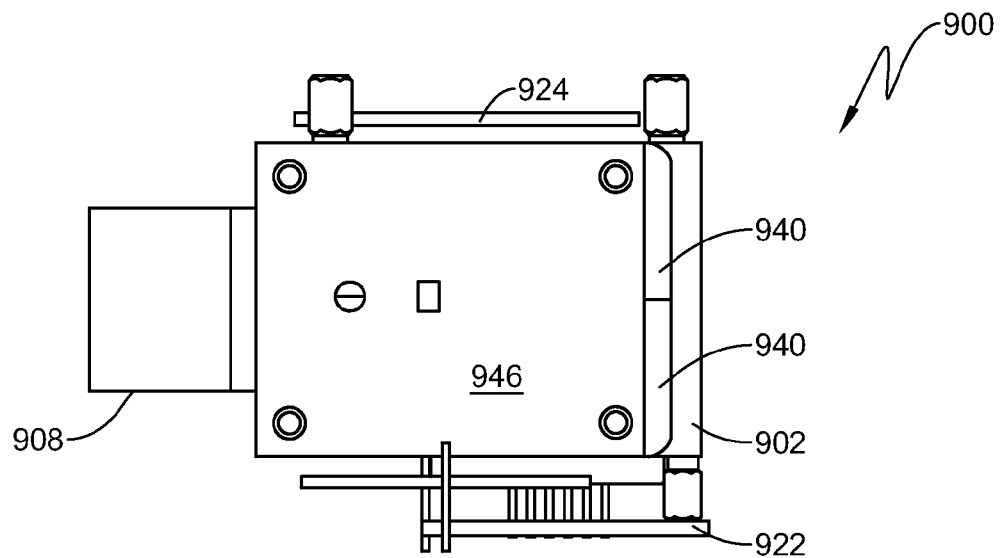
FIG. 22 is a top view of the device of the present invention shown in FIG. 18.
Figure 23:
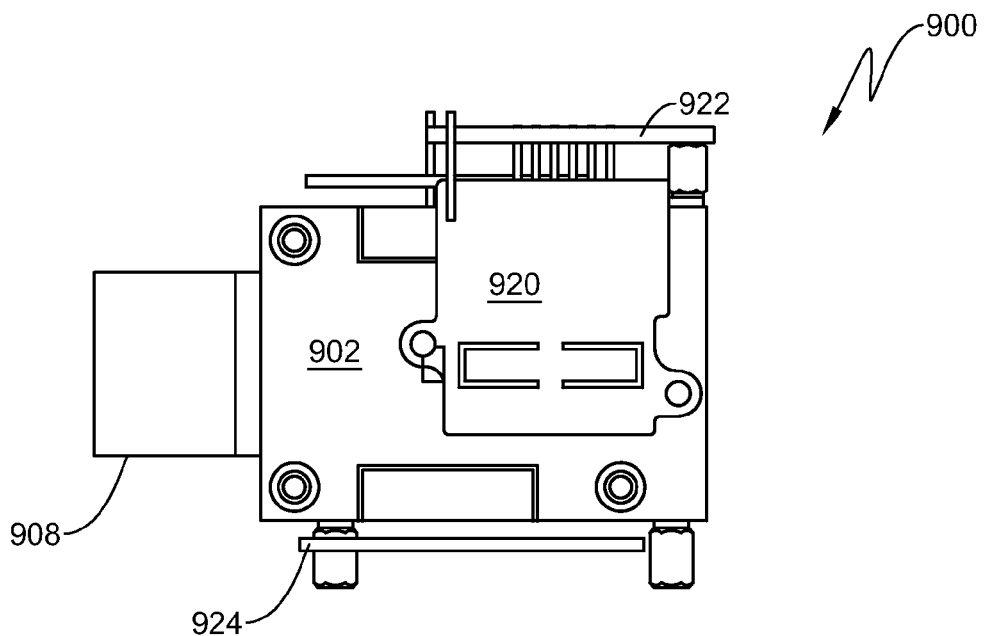
FIG. 23 is a bottom view of the device of the present invention shown in FIG. 18.

A similar embodiment of the present invention is shown in FIGS. 18 through 23. FIG. 18 is an isometric exploded view of a device 900 for aiding in the diagnosis of a respiratory dysfunction, and FIG. 19 is a cross-sectional view of the same. FIGS. 20 and 21 are an inlet and an outlet view of the device 900, respectively, and FIGS. 22 and 23 are a top and a bottom view of the same. The device 900 of the present invention, like that in the previous embodiment, employs a pair of bypass channels for the oxygen and flow sensors, thus eliminating the need for any mechanical light restrictors or labyrinths.

The device 900 generally includes a body portion 902 defining an airway 914 and a passage 912 configured for a carbon dioxide sensor emitter 932. The body portion 902 is preferably designed to receive an inlet adapter 908 at an inlet end and an outlet adapter 906 at an outlet end. As in previous embodiments, a flow restrictor 904 is disposed in the airway 914 for directing a selected portion of the airflow into the respective bypass channels. A flow sensor PCB 920, including a flow sensor 919, a first bypass channel 921 and the requisite electronics and circuitry, is attachable to the bottom of the body portion 902. As in previous embodiments, the first bypass channel 921 cooperates with the flow restrictor 904 to divert a portion of the airflow to the flow sensor 919, the resulting signal being adapted for transmission and processing by a controller 50 as part of the system 100 of the present invention.

The oxygen sensor PCB 944, including the oxygen sensor 945 and any associated electronics and circuitry, is disposable on the top of the body portion 902. Optionally, a shield 946 may be disposed above the oxygen sensor PCB 944 for protecting the circuitry and sensing components of the oxygen sensor 945 and its associated PCB. Although not shown in this embodiment, it should be understood that the preferred oxygen sensor 945 is similar to those previously described, including an emitter/detector pair in optical communication with an oxygen sensitive surface. The oxygen sensor PCB 944 is preferably disposable on or near a second bypass channel 942, which as shown herein is formed by a pair of top portions 940 that are conjoined over the body portion 902 as shown in FIG. 18. A pair of projections 948 are shown inserting into the airway 914, in communication with and forming portions of the second bypass channel 942. The projections 948 serve the dual purpose of filtering impurities and moisture from the air stream, as well as regulating the volume of air that is admissible into the second bypass channel for sensing by the oxygen sensor 945. As should be understood by those skilled in the art, the particular formation of the second bypass channel 942 utilizing the projections 948 shown herein is merely exemplary, and other methods and designs are equally well suited for achieving the following benefits.

As noted before, positioning of the oxygen sensor 945 in communication with the second bypass channel 942 provides a number of benefits, most notably simplifying the design and implementation of the present invention by obviating the need for mechanical light restrictors. Moreover, by securing the oxygen sensitive surface on the interior of a dark structure, the life and performance of the oxygen sensor 945 will not suffer due to the influence of ambient light. Also, by eliminating light restrictors, the overall volume of the airway 914 is decreased, therefore reducing the volume per breath needed in order to properly and consistently operate the sensors of the present invention. As noted throughout the current specification, it is a feature of the present invention that greater control and measurement precision over the relevant variables (flow, temperature, oxygen, carbon dioxide, and pulse rate) is instrumental in assuring accurate and predictive diagnosis of a respiratory dysfunction. Accordingly, by minimizing the volume necessary to induce performance of the sensors, the present invention results in more accurate and consistent measurements of the necessary parameters.

As in prior embodiments, the device 900 includes a carbon dioxide sensor that is disposable on either side of the body portion 902 in the form of a carbon dioxide sensor emitter PCB 924, including a carbon dioxide sensor emitter 932, and a carbon dioxide sensor detector PCB 922, including a carbon dioxide sensor detector 936. A series of couplers 930 connect the carbon dioxide sensor emitter 932 to its respective PCB, and a series of couplers 936 connect the carbon dioxide sensor detector 934 to its respective PCB. As in the previous embodiments, the carbon dioxide PCB's include all of the necessary electronics and circuitry for converting an optical signal into an electrical signal suitable for transmission to a controller 50 part of the system 100 described previously.

A thermometer 950 is also shown in fluid communication with the airway 914 for measuring a temperature of the air passing there through. Although not shown, the embodiment of the device 900 described herein is also adapted for utilizing a temperature control means of the type previously described.

Figure 24:
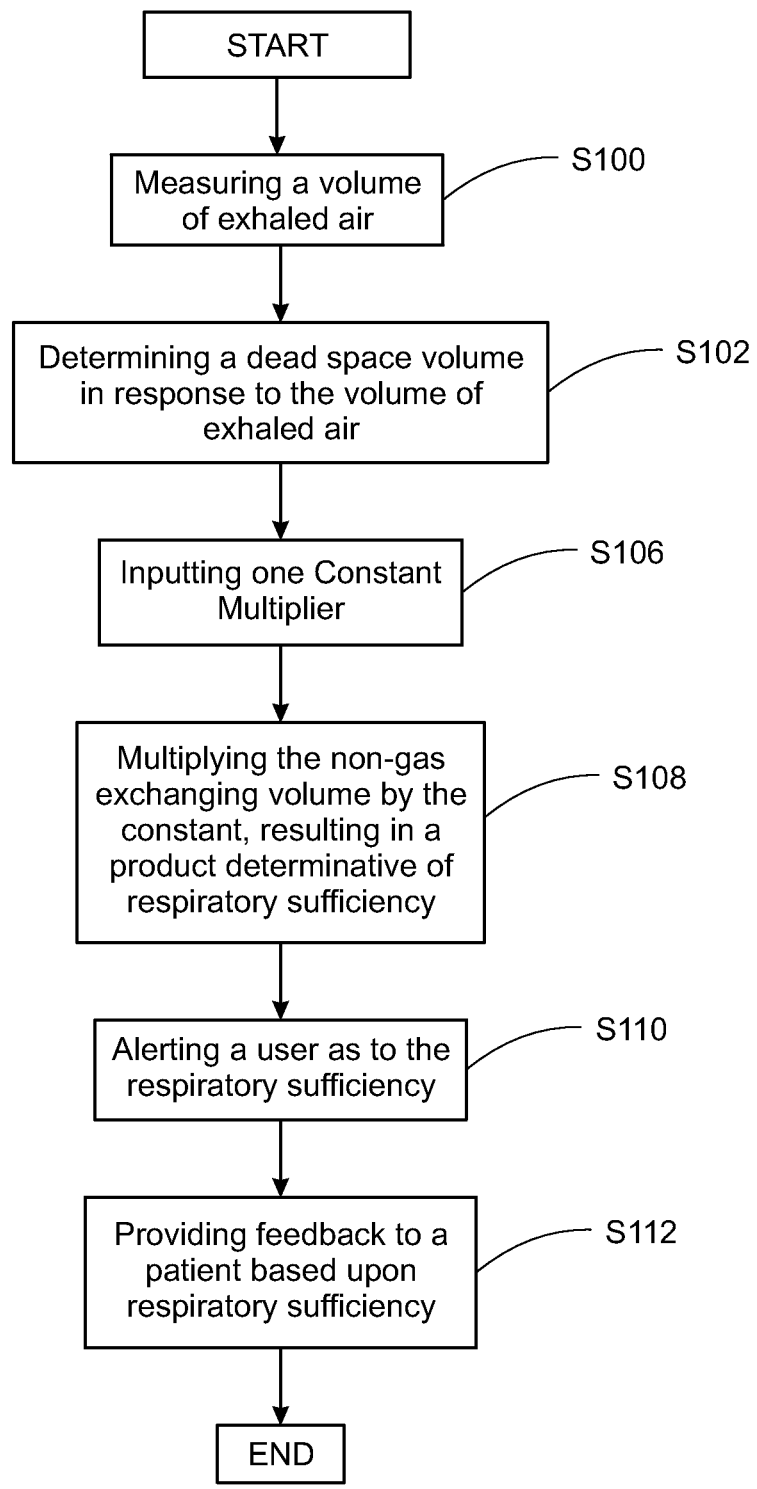
FIG. 24 is a flowchart depicting a method for determining the sufficiency of respiration in accordance with the present invention.

Turning to FIG. 24, a method for determining the sufficiency of respiration is provided according to the present invention. As noted with respect to prior aspects of the present invention, one of the many important factors in accurately measuring the oxygen content of a patient's exhaled air is the volume of expired air that is provided to the various sensors described above. A patient that does not have fully functional alveoli may not exhale sufficiently to properly and consistently measure the content of his or her exhaled breathe, as the gas-exchanging process within the patient's lungs may be degraded. Accordingly, the present invention includes a method for determining whether any exhaled breath passed through the systems and devices described above is sufficient for diagnostic purposes.

Step S100 of the method includes measuring a volume of exhaled air. As noted above, the flow sensor of the present invention, operating in concert with the temperature control features of the present invention, is adapted for providing such a measurement.

In step S102, the method recites determining a dead space volume in response to the volume of exhaled air. As is known in the art, the dead space volume refers to the portion of any tidal breath where gas exchange does not take place. There are numerous methodologies known in the art for determining the dead space volume, including for example the Fletcher-Fowler method. The Fletcher-Fowler method includes measuring a carbon dioxide concentration across an exhalation period, resulting in a curve representing the exhaled volume as a function of carbon dioxide concentration. Integration of the curve about an equilibrium point results in the calculation of a dead space volume, which may or may not be indicative of a respiratory dysfunction such as pulmonary embolism.

In step S106, the method recites inputting a constant multiplier, preferably between 1.5 and 1.9, and even more preferably between 1.6 and 1.8. In more preferred embodiments of the present invention, the constant multiplier is approximately 1.7. In step S108, the non-gas exchanging volume is multiplied by the constant multiplier, resulting in a product that is determinative of respiratory sufficiency. For example, if the resulting product is greater than a predetermined value, then the exhalation was insufficient for diagnostic purposes. On the contrary, if the resulting product is less than the predetermined value, then the exhalation was sufficient for diagnostic purposes and the system and device of the present invention will have a sufficient volume of air for accurate and consistent measurements.

In step S110, the method recites the step of altering the user as to the respiratory sufficiency. In preferred embodiments, this alert may be practiced through automated means such as a visual or aural signal emanated by the system or device of the present invention. For example, the display described above with reference to the system of the present invention may be adapted for signaling to a user the resulting product in a visual form, such as a green light for a sufficient breath and a red or yellow light for an insufficient breath. Many similar methods and modes of altering the user can be readily devised by those skilled in the art. Following the alert, the method includes step S112 that recites providing feedback to a patient based upon respiratory sufficiency. Preferably, this step includes coaching a patient to breath more deeply or exhale more completely in the case of an insufficient respiration. As in the previous step of the method, step S112 can be readily automated and performed by the system and device of the present invention described above.

Figure 25:
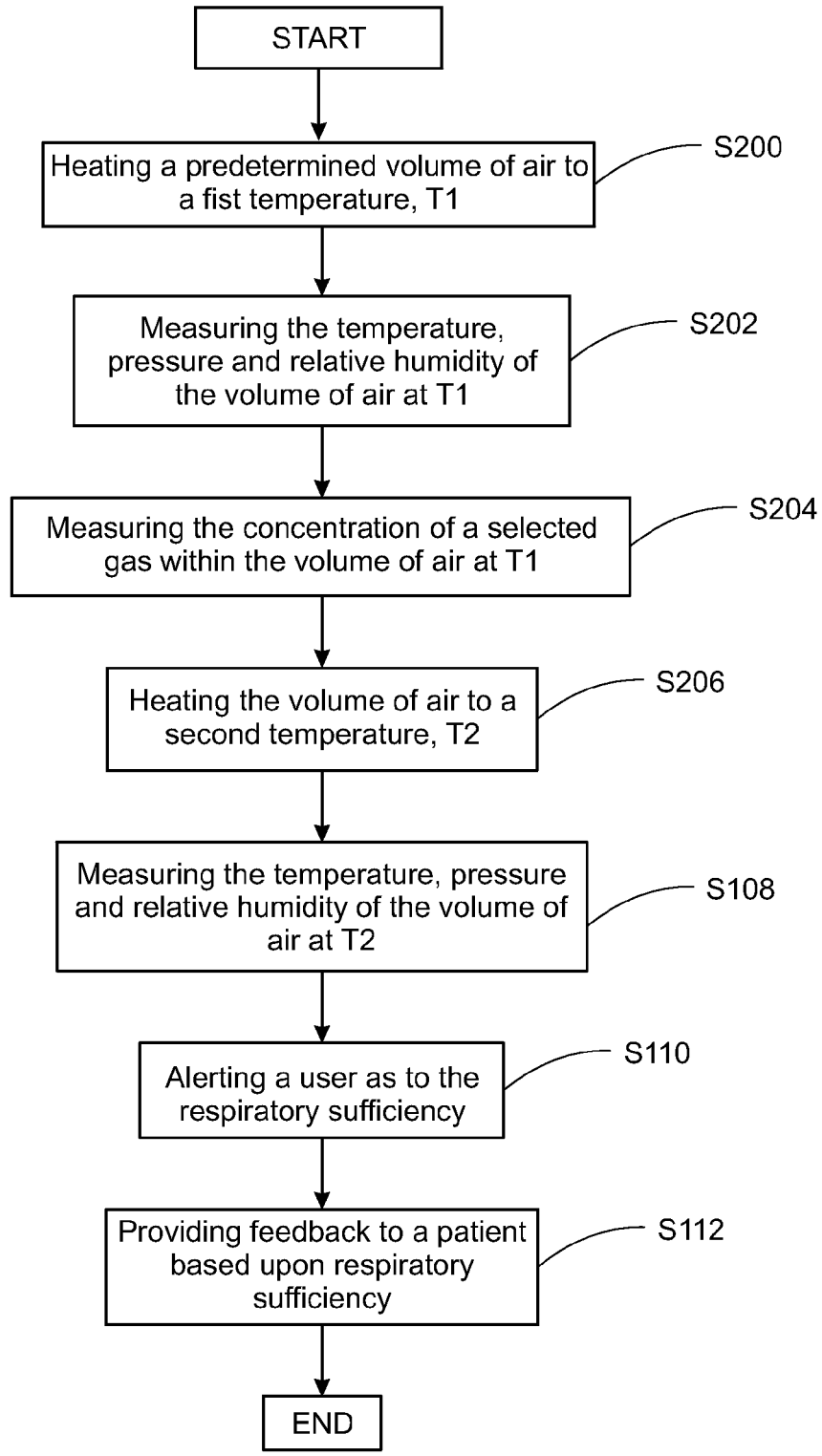
FIG. 25 is a flowchart depicting a method for calibrating a gas sensor in accordance with the present invention.

FIG. 25 is a flowchart depicting a method for calibrating a gas sensor in accordance with the present invention. As noted with respect to the system and device of the present invention, the optimal performance of the sensors depends heavily on the environment in which the measurements are taken. Those skilled in the art will recognize that Boyle's law, PV=nRT, wherein the pressure, volume, molecular concentration and temperature of the airflow through the system and device of the present invention are all interrelated. As such, proper measurement of any concentration of a gas preferably incorporates a simultaneous measurement of the temperature, as indicated with the incorporation of the temperature control systems and thermometers within the systems and devices described above. For any given volume and pressure of air, therefore, one can find an inverse relationship between the temperature T and the concentration n of a gas.

In step S200, the method recites the step of heating a predetermined volume of air to a first temperature, $T_1$. In preferred embodiments, the heating of the predetermined volume of air is accomplished by the temperature control means and associated controls within the device and system of the present invention. Step S202 recites measuring the temperature of the volume of air at $T_1$, and step S204 recites measuring the concentration of a selected gas, such as oxygen, within the volume of air at $T_1$. Accordingly, for a predetermined temperature $T_1$, the method provides for a measurement of the temperature and concentration of a selected gas, most preferably using the oxygen sensor of the system and device to measure an oxygen concentration within the volume of air.

In step S206, the volume of air is heated to a second temperature, $T_2$. In step S208, the method recites measuring the temperature of the volume of air at $T_2$. Step S210 recites measuring the concentration of the selected gas, preferably oxygen, at $T_2$. As such, for the second temperature $T_2$, the method provides for the measurement of the temperature and concentration of the selected gas within the same volume of air.

As evident from Boyle's law, any increase in temperature should not affect the molecular concentration of the selected gas provided that the volume of the sample is held constant. One would reasonably expect the pressure to increase, however, with an increase in temperature. Given the foregoing, the method includes step S212, which is calculating a variance between the concentration of the selected gas as measured at temperatures $T_1$ and $T_2$.

To the extent that there is a variation in the measured concentration, it must be indicative of a calibration issue with the sensor, as there can be no change in the concentration of a gas within a closed volume. Thus the method recites in step S214 correlating the concentration of the selected gas to a temperature in response to any calculated variance. As such, a user will be informed of the temperature dependence of the measurements provided by the sensor. For example, the performance of the optical oxygen sensor described herein is affected by temperature changes, and thus the methodology set forth above provides a user with the necessary relationship between the output signal of the sensor and the temperature as measured within the device and system.

Thus in step S216, the method provides for calibrating a sensor adapted to sense a concentration of the selected gas in response to its dependence on a temperature. The preferred method for calibration includes processing both temperature and sensor data as it is fed into a central controller, such as that described above with reference to the system of the present invention. Knowing the functional relationship between the temperature output and the gas sensor output permits a user to program or otherwise control the system to bias or vary the output of the gas sensor to provide a temperature-dependent, and thus more accurate, measurement of the concentration of the gas within a volume of air. Although oxygen is generally the selected gas, it should be understood that the method described herein is equally applicable to carbon dioxide or any other gaseous concentrations to be measured by the device and system of the present invention.

Moreover, it is also preferable to measure the pressure of the ambient air as well as the humidity of the ambient air, as these values may directly or indirectly affect the ability of the gas sensor to properly measure the concentration of the selected gas. Suitable devices for measuring the pressure and humidity of the ambient air are known in the art, and preferably signals indicative of the aforementioned conditions can be readily integrated into the system and methodology of the present invention.

Figure 26:
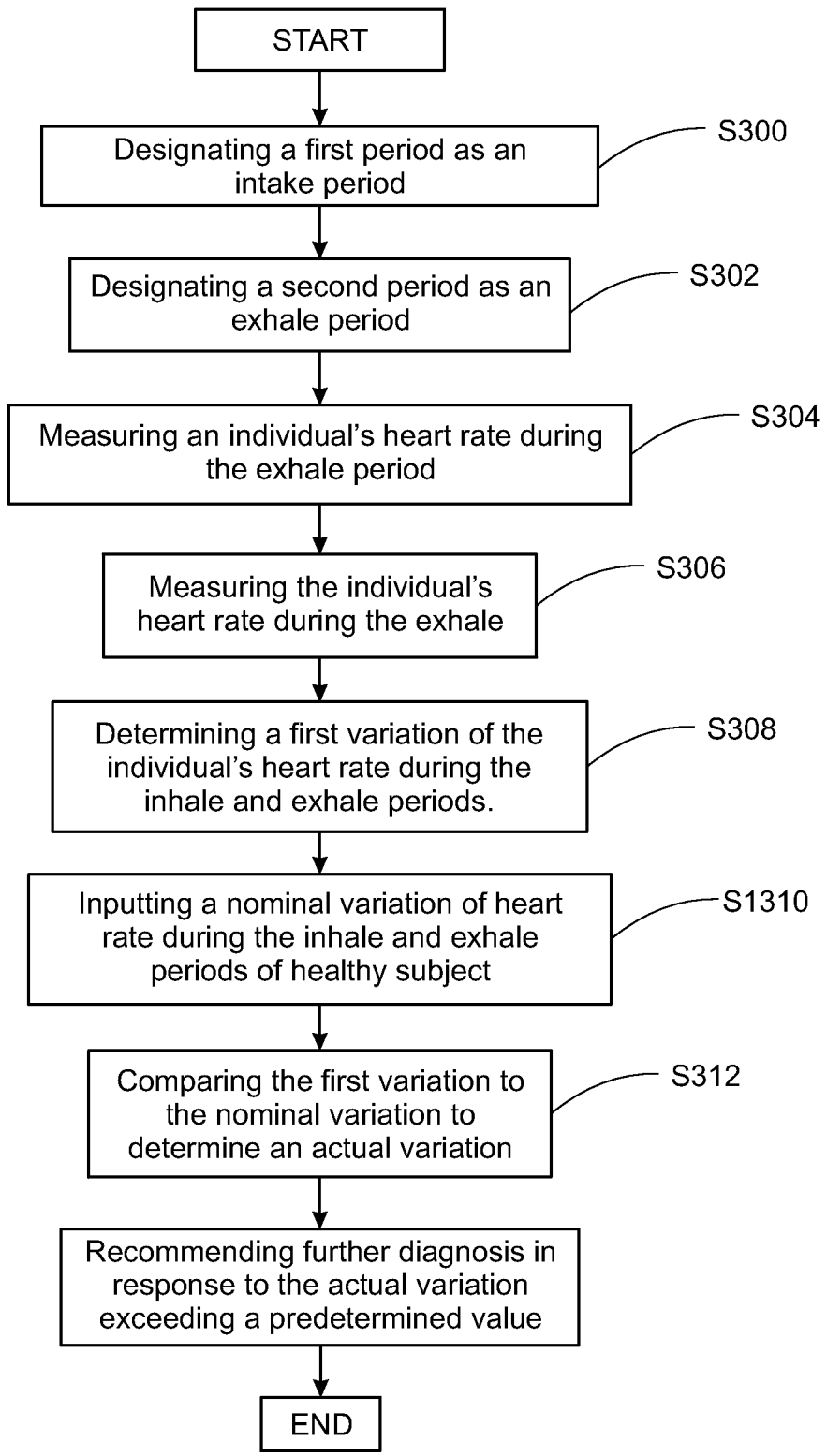
FIG. 26 is a method for aiding in the diagnosis of a respiratory dysfunction in accordance with the present invention.

Another method practicable according to the system and device of the present invention is shown in the flowchart of FIG. 26, which is a method for recommending further diagnostics in response to a variation in a user's heartbeat between an exhalation and an inhalation. In step S300, the method designates a first period as an inhalation period, and in step S302, the method designates a second period as an exhalation period. As described above, the system of the present invention includes a pulse meter or pulse-oximeter for measuring at least an individual's heart rate during the testing interval. As such, in step S304, the method recites measuring an individual's heart rate during the inhalation period; and step S306 includes measuring the individual's heart rate during the exhalation period.

In step S308, the method recites determining a first variation of the individual's heart rate during the inhalation and exhalation periods. It is anticipated that there will be some variation in heart rate, as this is the normal result from a healthy individual. As such, in step S310, the method recites inputting a nominal variation of a heart rate during the inhalation and exhalation periods that is representative of the variation for a healthy subject. In step S312, the method includes comparing the first variation to the nominal variation to determine an actual variation, i.e. wherein the presence of an actual variation is indicative of an abnormality in the individual's cardio-pulmonary system. In response to an actual variation that exceeds a predetermined value, for example outside the margin of error of the nominal and first variations, step S314 recites the step of recommending that further diagnostics be done on the individual. Said further diagnostics may include any and all of the testing of gaseous concentrations of exhaled breath as well as any other test or measurements that may aid in the diagnosis of a respiratory dysfunction such as pulmonary embolism.

The present invention has been described herein with reference to its most preferred and exemplary embodiments with reference to the noted figures. However, it should be apparent to those skilled in the art that numerous deviations from the described embodiments can be readily devised without departing from the scope of the present invention as defined in the following claims.

What is claimed is:

1. A device for aiding in the diagnosis of a respiratory dysfunction, the device comprising an airway defining a longitudinal axis and having an inlet and an outlet through which a user breathes, the device comprising:
   a stationary flow restrictor for restricting the flow of air disposed within the airway, the restrictor comprising a plurality of openings and occlusions, the restrictor effective for causing a buildup of air pressure in the airway and oriented such that each inhaled and exhaled breath of air passing through the airway is diverted in part out of the airway and into a sensor disposed in a first bypass channel adjacent to the airway and in fluid communication with the airway, wherein portions of each inhaled and exhaled breath of air simultaneously pass through the airway and the first bypass channel, wherein the airway defines a first pair of ports through which air may be diverted from the airway into the first bypass channel at an airtight junction; and
   a second bypass channel adjacent to the airway and in fluidly connected to the airway,
   wherein the airway defines a second pair of ports through which air may be diverted from the airway into the second bypass channel at an airtight junction,
   wherein the second bypass channel houses an oxygen sensor therein and/or thereon for measuring the concentration of oxygen in a breath to aid in the determination of respiratory dysfunction, and
   wherein the stationary flow restrictor disposed within the airway directs a portion of the flow of air out of the airway and into the second bypass channel.

2. The device of claim 1, further comprising a carbon dioxide sensor disposed within the airway for measuring a concentration of carbon dioxide in an exhaled breath for aiding in the determination of respiratory dysfunction.

3. The device of claim 2 wherein the carbon dioxide sensor is an optical sensor including a light emitting diode.

4. The device of claim 2, further comprising an oxygen sensor disposed with the airway, wherein the oxygen sensor and the carbon dioxide sensor are substantially perpendicular to one another within the airway, and wherein the oxygen sensor measures a concentration of oxygen in an exhaled breath for aiding in the determination of respiratory dysfunction.

5. The device of claim 4 wherein the oxygen sensor is an optical sensor including a light emitting diode.

6. The device of claim 1 wherein the oxygen sensor is an optical sensor including a light emitting diode disposed on a first side of the second bypass channel though which air may flow.

7. The device of claim 6, further comprising a coated surface disposed opposite the light emitting diode on a second side of the second bypass channel such that light emitted from the light emitter is incident upon the coated surface, the coated surface being optically sensitive to the presence of oxygen.

8. The device of claim 1 further comprising a controller for determining a concentration ratio of oxygen to carbon dioxide in an exhaled breath.

9. The device of claim 8, further comprising a temperature sensor in communication with the controller wherein the temperature sensor measures the temperature of inhaled air and exhaled air.

10. The device of claim 9 wherein the controller determines a concentration ratio of oxygen to carbon dioxide in an exhaled breath based at least in part upon the temperature of the inhaled air and exhaled air.

11. The device of claim 1 further comprising a thermal control element wherein the thermal control element measures temperature within the airway and heats the airway to an optimum temperature at which one or more sensors may monitor respiratory dysfunction wherein the thermal control element.

12. The device of claim 11 wherein the thermal control element comprising:
    a heating element that heats the airway to a predetermined minimum temperature sufficient to prevent condensation of water vapor in an exhaled breath; and
    at least one thermometer disposed within the device for determining a temperature of air passing through the device,
    wherein the thermal control system is in communication with a temperature control mechanism, and
    wherein the temperature control mechanism monitors the thermometer output and maintains the heating element at a minimum temperature sufficient to prevent condensation of water vapor in exhaled breath, thereby protecting the one or more sensors from condensation interference during monitoring of parameters indicative of respiratory dysfunction.

13. The device of claim 11 wherein the heating element comprising a resistive heating element coupled to a power source.

14. The device of claim 11 wherein the temperature control mechanism is configured to maintain the heating element at a temperature in the range of thirty-three and forty-three degrees Celsius.

15. The device of claim 11 wherein the temperature control mechanism is configured to maintain the heating element at a temperature of thirty-eight degrees Celsius and wherein the air flowing through the airway has a uniform temperature profile.

16. The device of claim 11 wherein the heating element is positioned within or adjacent the walls defining the airway for the purpose of heating the airway.

17. A device for aiding in the diagnosis of a respiratory dysfunction, the device including an airway defining a longitudinal axis and having an inlet and an outlet through which a user breathes, the device comprising:
   a stationary flow restrictor for restricting the flow of air disposed within the airway, the restrictor comprising a plurality of openings and occlusions, wherein the restrictor causing a buildup of air pressure in the airway and oriented such that each inhaled and exhaled breath of air passing through the airway is diverted in part out of the airway and into a first sensor disposed in a first bypass channel adjacent to the airway and a second sensor disposed in a second bypass channel adjacent to the airway, such that portions of each breath of inhaled and exhaled air simultaneously pass through the airway and the first and second bypass channel, wherein the airway defines a first pair of ports through which air may be diverted from the airway into the first bypass channel at an airtight junction and wherein the airway defines a second pair of ports through which air may be diverted from the airway into the second bypass channel at an airtight junction.

18. The device of claim 17 further comprising a controller adapted to communicate with the plurality of sensors, wherein the controller monitors sensor output for the presence of respiratory dysfunction.

19. The device of claim 17 further comprising a thermal control element, wherein the thermal control element measures temperature within the airway and heats the air in the device to an optimum temperature at which the plurality of sensors may monitor respiratory dysfunction.

20. The device of claim 19 wherein the thermal control element comprising:
   a heating element that heats the airway to a predetermined minimum temperature sufficient to prevent condensation of water vapor in an exhaled breath; and
   at least one thermometer disposed within the device for determining a temperature of air passing through the device,
   wherein the thermal control system is in communication with a temperature control mechanism, and
   wherein the temperature control mechanism monitors the thermometer output and maintains the heating element at a minimum temperature sufficient to prevent condensation of water vapor in exhaled breath, thereby protecting the plurality of sensors from condensation interference during monitoring of parameters indicative of respiratory dysfunction.

* * * * *